(12) United States Patent
Lucas

(10) Patent No.: US 7,285,530 B2
(45) Date of Patent: Oct. 23, 2007

(54) USE OF SERP-1 AS AN ANTIPLATELET AGENT

(75) Inventor: Alexandra Lucas, London, ON (CA)

(73) Assignee: Viron Therapeutics, Inc., London, Ontario (CA)

( * ) Notice: Subject to any disclaimer, the term of this patent is extended or adjusted under 35 U.S.C. 154(b) by 60 days.

(21) Appl. No.: 11/256,257

(22) Filed: Oct. 21, 2005

(65) Prior Publication Data

US 2006/0122115 A1 Jun. 8, 2006

Related U.S. Application Data

(60) Provisional application No. 60/620,786, filed on Oct. 21, 2004.

(51) Int. Cl.
*C07K 14/00* (2006.01)
(52) U.S. Cl. .......................... 514/2; 530/350; 435/183
(58) Field of Classification Search ................... 514/2; 530/350; 423/183
See application file for complete search history.

(56) References Cited

U.S. PATENT DOCUMENTS

| 5,686,409 A | 11/1997 | McFadden et al. |
| 5,917,014 A | 6/1999 | McFadden et al. |
| 5,939,525 A | 8/1999 | McFadden et al. |

OTHER PUBLICATIONS

Jiang et al., 1997; Characterization and functional analysis of 12 naturally occurring reactive site variants of serpin-1 from Manduca sexta. J. Biol. Chem 272(2): 1082-1987.*
Zalia, C. V. et al., "Increased Circulating Monocyte Activation in Patients With Unstable Coronary Syndromes", *Journal of the American College of Cardiology*, 38(5): 1340-1347 (2001).
Nash, P. et al., "Inhibitory Specificity of the Anti-Inflammatory Myxoma Virus Serpin, SERP-1", *The Journal of Biological Chemistry*, 273(33): 20982-20991 (1998).
Lomas, D. A. et al., "Inhibition of Plasmin, Urokinase, Tissue Plasminogen Activator, and $C_{is}$ by a Myxoma Virus Serine Proteinase Inhibitor", *The Journal of Biological Chemistry*, 268(1): 516-521 (1993).
Lucas, A. et al., "Virus-Encoded Serine Proteinase Inhibitor SERP-1 Inhibits Atherosclerotic Plaque Development After Balloon Angioplasty", *Circulation*, 94: 2890-2900 (1996).
Lucas, A. et al., "Transplant Vasculopathy: Viral Anti-Inflammatory Serpin Regulation of Atherogenesis", *J. Heart Lung Transplant.*, 19: 1029-1038 (2000).
Miller, L. W. et al., "Inhibition of Transplant Vasculopathy in a Rat Aortic Allograft Model After Infusion of Anti-Inflammatory Viral Serpin", *Circulation*, 101: 1598-1605 (2000).

Bot, I. et al., "Serine Protease Inhibitor Serp-1 Strongly Impairs Atherosclerotic Lesion Formation and Induces a Stable Plaque Phenotype in ApoE$^{-/-}$ Mice", *Cir. Res.*, 93: 464-471 (2003).
Brahn, E. et al., "Suppression of Collagen-Induced Arthritis With a Serine Proteinase Inhibitor cloned From a Myxoma Viral Sequence", *American College of Rheumatology Meeting*, Nov. 13-17, 1999, Abstract.
Bedard, E. et al., "Viral Proteins: A Novel Approach to Preventing Chronic Rejection", *American Society of Transplant Surgeons* (2002), Abstract.
Wang, H. et al., "Serp-1, a viral anti-inflammatory serpin, attenuates acute xenograft rejection in a rat-to-mouse cardiac transplant model", *7th International Congress of Xenotransplantation* (2003), Abstract.
Dai, E. et al., "Serp-1, a Viral Anti-inflammatory Serpin, Regulates Cellular Serine Proteinase and Serpin Repsonses to Vascular Injury", *The Journal of Biological Chemistry*, 278(20): 18563-18572 (2003).
Viswanathan, K. et al., "Serpins—A Link Between The Thrombolytic and Innate Immune Response Pathways", *Scientific Session of the American Heart Association Meeting*, Nov. 7-10, 2004, Abstract.
Viswanathan, K. et al., "Serpins—A Link Between The Thrombolytic and Innate Immune Response Pathways", *Canadian Cardivascular Congress*, Oct. 23-27, 2004, Abstract.
Viswanathan, K. et al., "The Anti-inflammatory Viral Serpin Serp-1, Inhibits Human Monocyte Cell Activation", *Sixth World Congress on Inflammation Meeting*, Aug. 2-6, 2003, Abstract.
Viswanathan, K. et al., "Serp-1, A Viral Anti-Inflammatory and Anti-Atherogenic Protein Sequentially Alters Membrane Fluidity in Activated Human Atherogenic Cells", *Canadian Cardiovascular Congress*, Oct. 24-29, 2003, Abstract.
Lucas, A. et al., "Regulation of Vascular Innate Immune Responses by Viral and Mammalian Serpins", *XIII International Vascular Biology Meeting*, Jun. 1-5, 2004, Abstract.
Dai, E. et al., "Evaluation of the Effects of Viral Serpin Infusion on Plaque Growth After Aortic Transplant Using PAI-1-/- Mouse Model", *Canadian Cardiovascular Congress*, Oct. 24-29, 2003, Abstract.
Dai, E. et al., "Viral Serpin Regulation of Transplant Vasculopathy Development", *Canadian Cardiovascular Congress*, Oct. 26-30, 2002, Abstract.

* cited by examiner

*Primary Examiner*—Karen Cochrane Carlson
(74) *Attorney, Agent, or Firm*—Scully, Scott, Murphy & Presser, P.C.

(57) ABSTRACT

Compositions and methods for antiplatelet/anti-thrombotic therapy in a mammalian subject are provided. The method involves administering a therapeutically effective amount of SERP-1 admixed with a pharmaceutically acceptable carrier to a subject in need of such therapy. Methods of administering SERP-1 with at least one other antiplatelet agent are also provided. The compositions and methods of the present invention are useful for treating and preventing recurrence of numerous cardiovascular diseases and injuries.

5 Claims, 18 Drawing Sheets

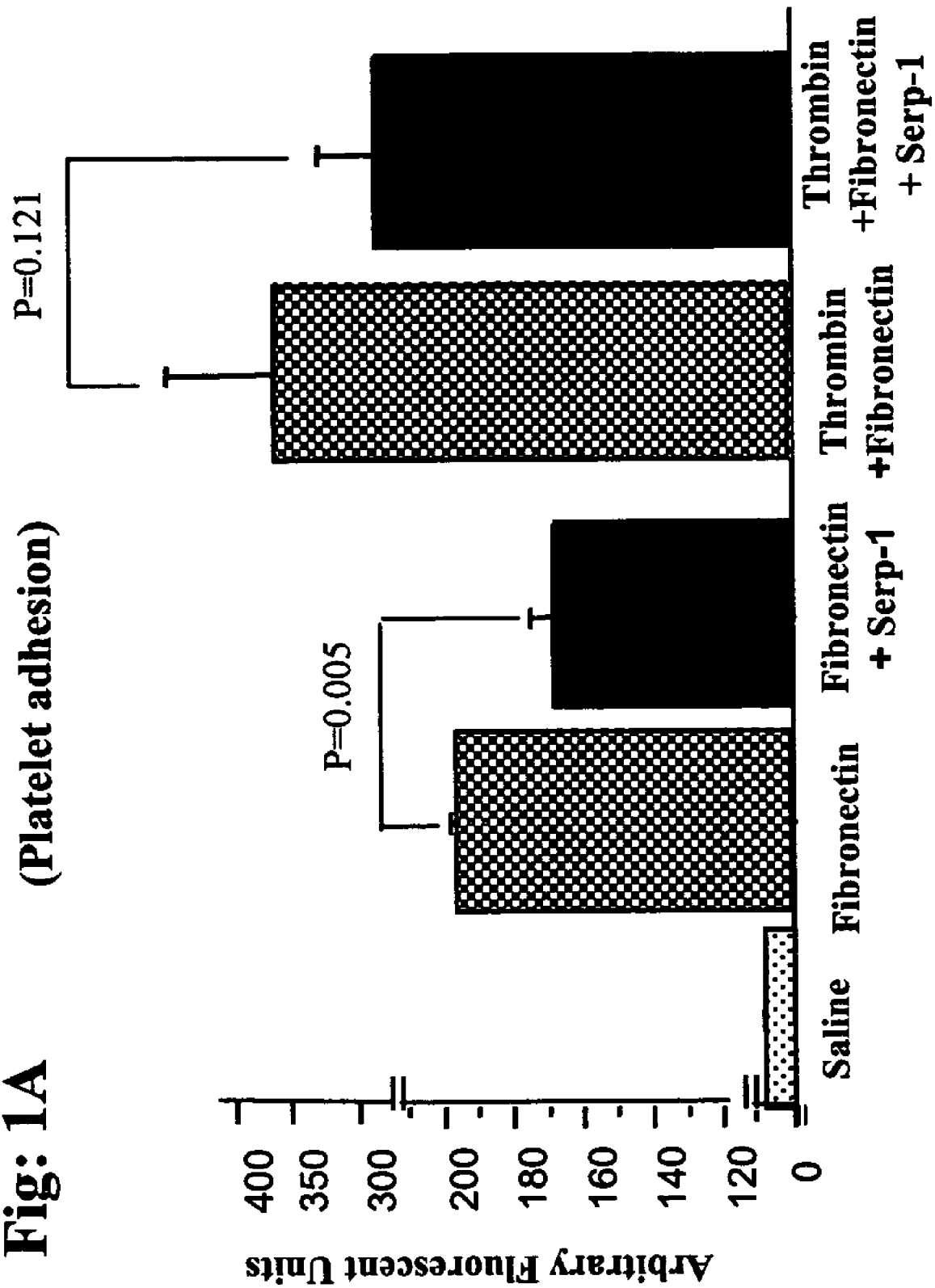

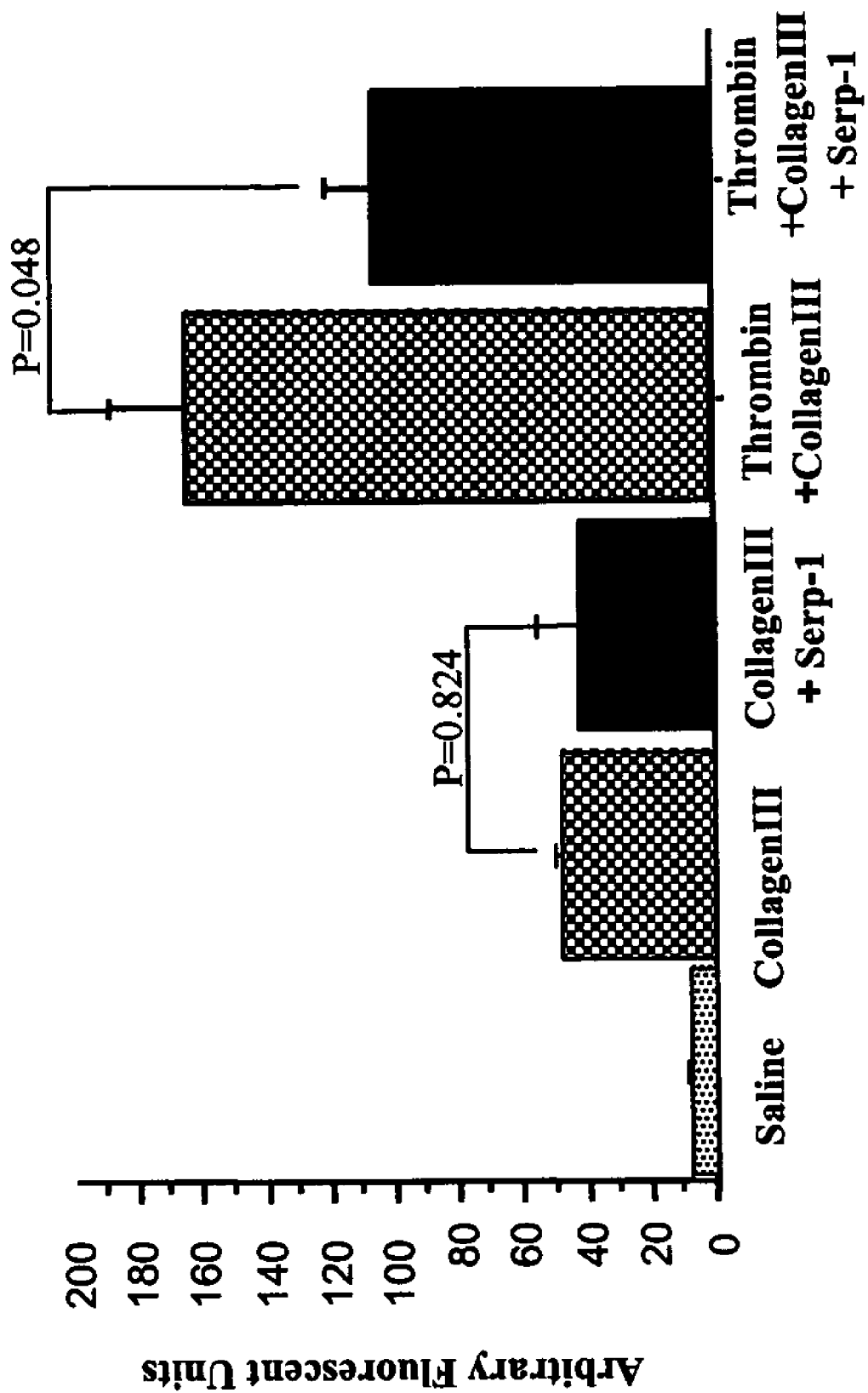

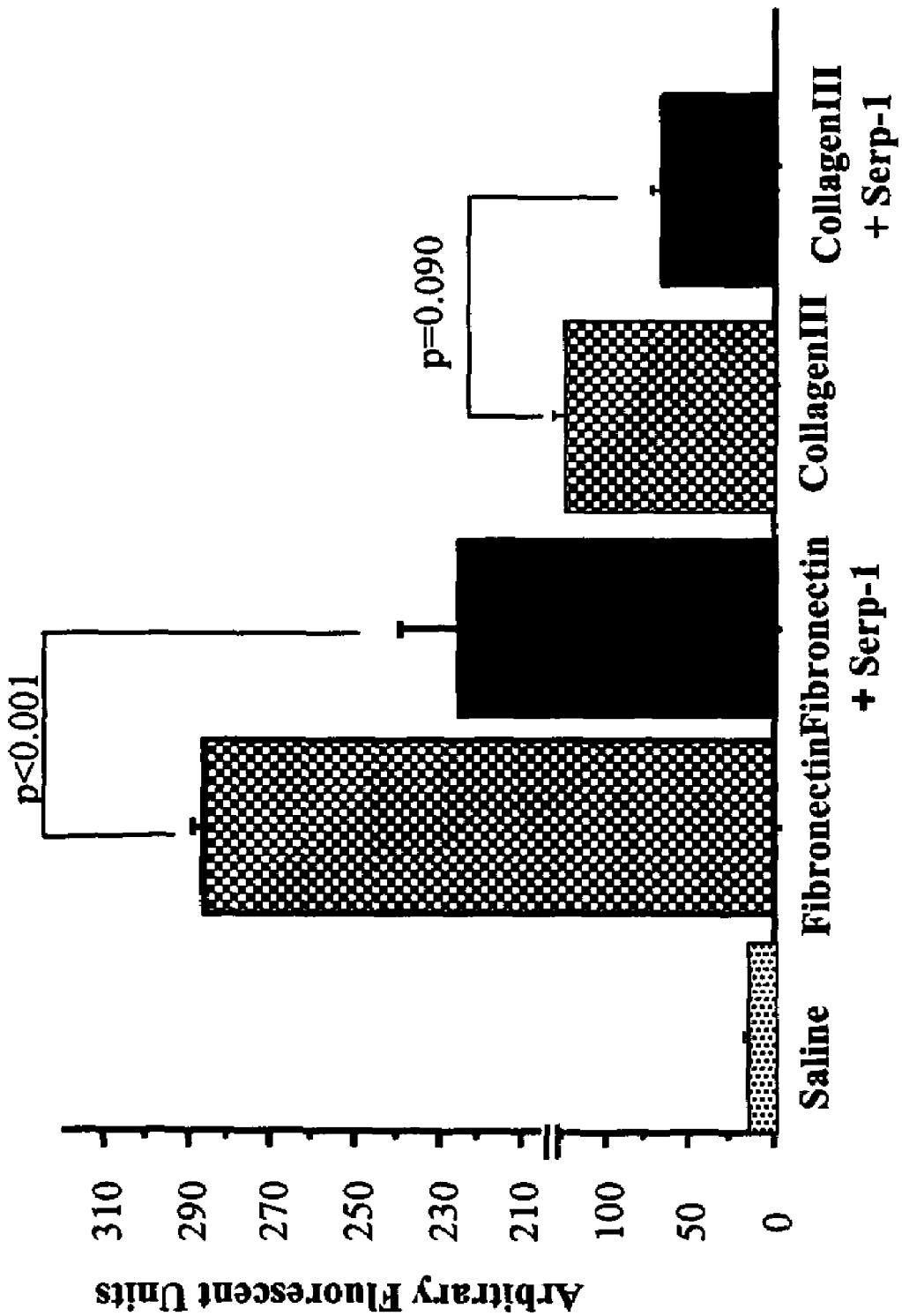

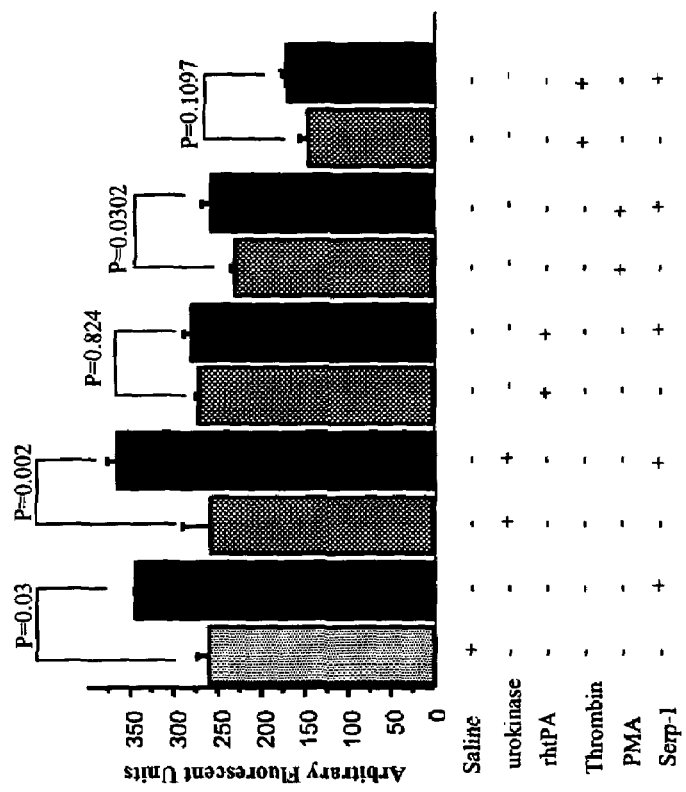

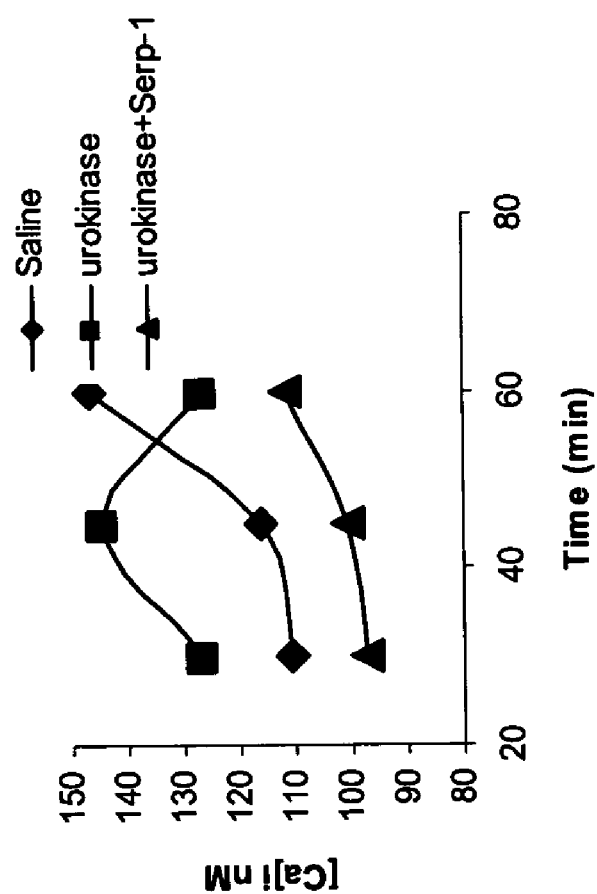

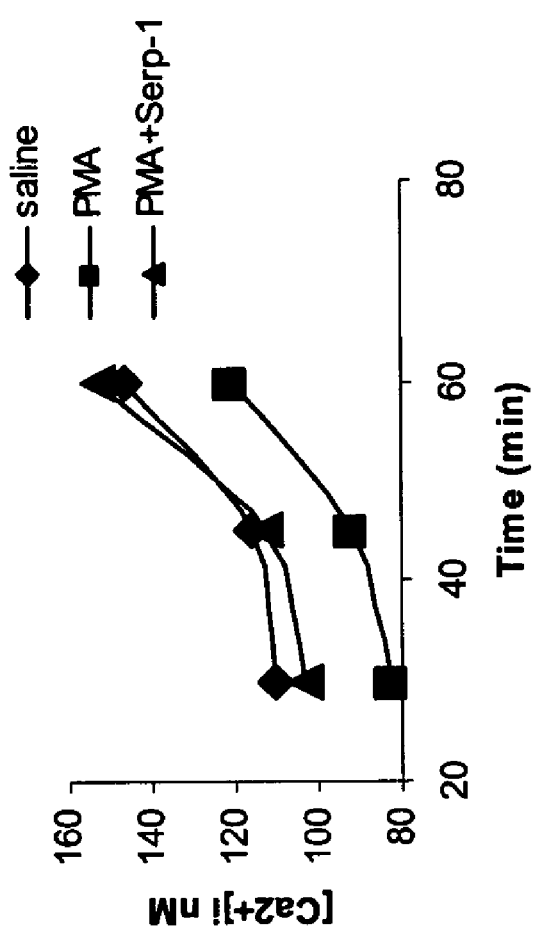

THP-1 [Ca$^{2+}$]$_i$ Kinetics

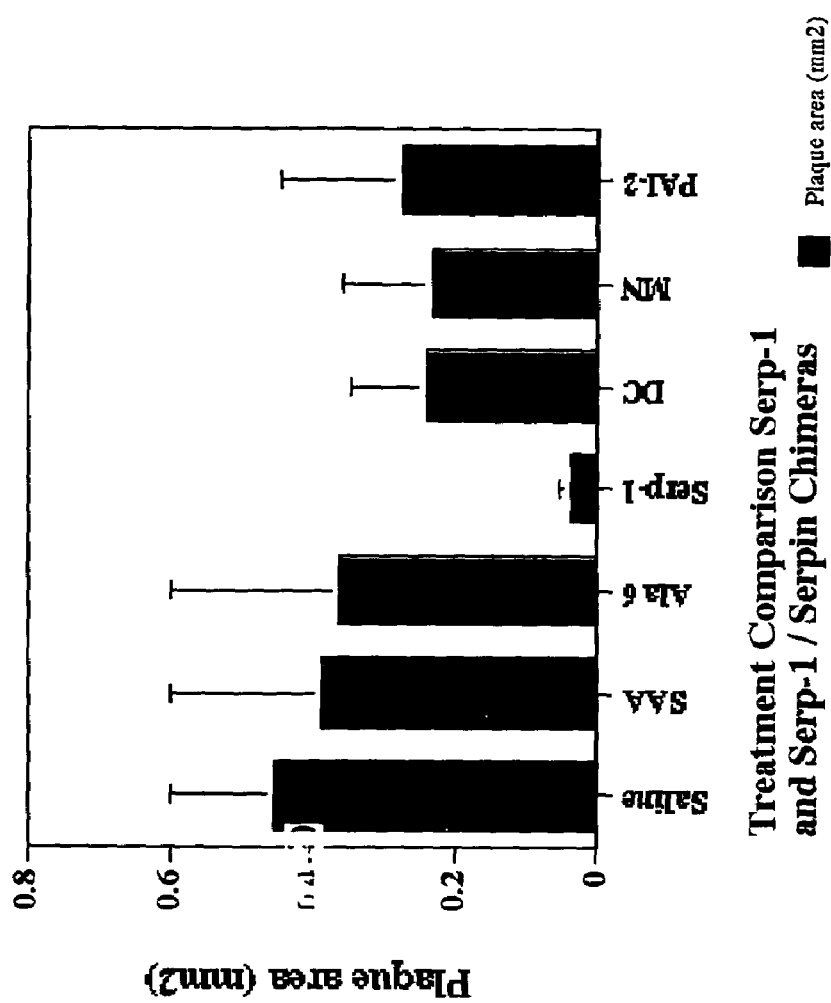

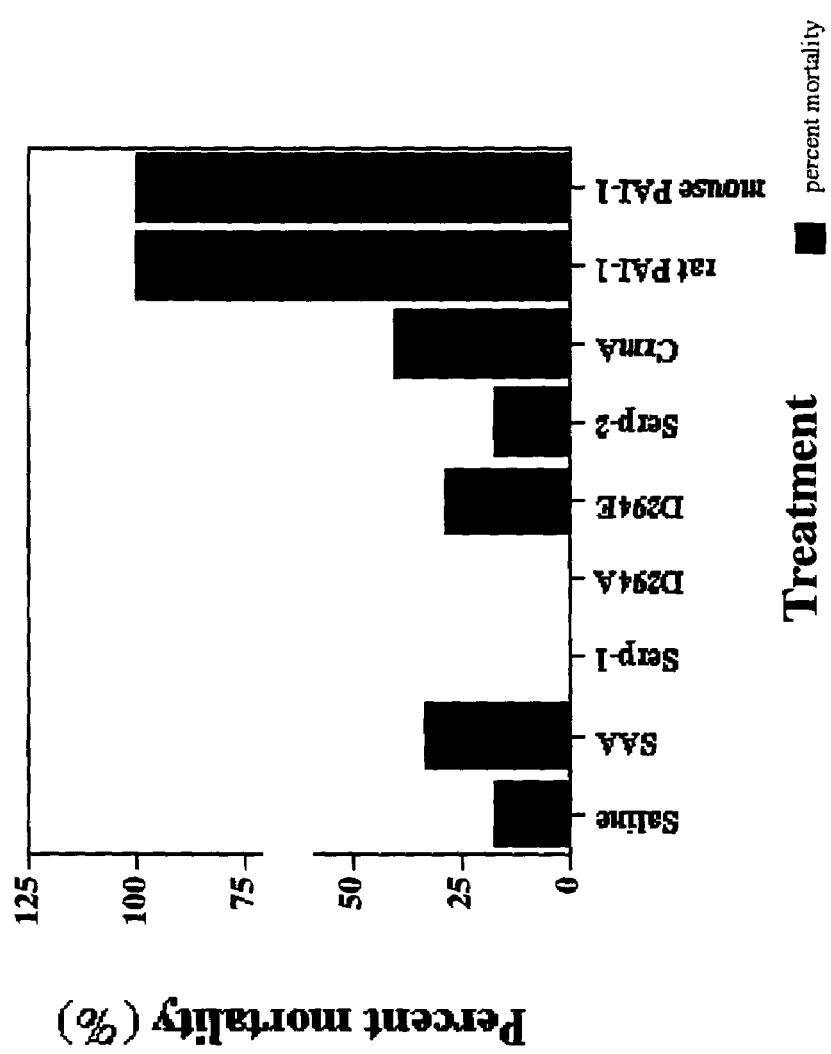

USE OF SERP-1 AS AN ANTIPLATELET AGENT

CROSS REFERENCE TO RELATED APPLICATION

This application claims the benefit of U.S. Provisional Application No. 60/620,786, filed Oct. 21, 2004.

FIELD OF THE INVENTION

The present invention relates generally to the fields of cardiology, hematology, and related disorders. The invention specifically relates to a viral protein, SERP-1, its analogs and biologically active fragments. Particularly, the present invention relates to the ability of SERP-1, its analogs and biologically active fragments to block platelet adhesion and activation. The invention also relates to the use of the antiplatelet or antithrombotic activity of SERP-1, its analogs and biological fragments for antiplatelet therapy in mammals.

BACKGROUND OF THE INVENTION

Cardiovascular disease (CVD) takes many forms. Heart attacks are only one form of cardiovascular disease. Others include hypertension (high blood pressure), coronary artery disease, rheumatic heart disease, stroke, and peripheral vascular disease with gangrene. According to the American Heart Association, CVD has been the No. 1 killer in the United States every year since 1900 but 1918. Nearly 2,600 Americans die of CVD each day, an average of 1 death every 34 seconds. CVD claims more lives each year than the next 5 leading causes of death combined, which are cancer, chronic lower respiratory diseases, accidents, diabetes mellitus, and influenza and pneumonia. American Heart Association, *Heart Disease and Stroke Statistics*—2004 *Update*, page 3 (http://www.americanheart.org).

In 2004, the estimated direct and indirect cost of CVD is $368.4 billion. CVD does not only occur in adults. Atherosclerosis and other heart diseases, such as stroke, are serious and largely unrecognized problems that affect thousands of children.

Platelets, which are small cell derived bodies that normally circulate in the bloodstream, help the body defend itself against bleeding and blood loss. They function by sticking to the vessel surface and aggregating (sticking together) and helping in the formation of a clot at the site of bleeding. The process of creating a blood clot, which is called thrombosis, is beneficial to a person with severe bleeding. However, blood clots can also cause severe problems, particularly when they form in the vessels of the heart or brain.

Under normal healthy conditions, the different cellular components of flowing blood (such as red and white blood cells and platelets) are unable to stick to the inner lining of blood vessels and cause a blockage that disrupts blood flow. However, when there is injury to the inner lining of blood vessels, such as caused by injurious pulsatile flow, coronary artery stent placement, buildup of fatty deposits, or connective tissue and cellular proliferation (atherosclerosis) within blood vessels, the lining of the vessels (the endothelium) is less resistant to the formation of dangerous blood clots. As a result of the injury, platelets in the circulating blood begin to accumulate, along with isolated monocytes and macrophage/foam cells (lipid filled macrophages), and begin to accumulate excess cholesterol, fats, and connective tissue (collagen and aelastin). Cholesterol, fat and other inflammatory substances (cytokines and chemokines) are also attracted to minor injuries in arterial walls that arise from high blood pressure.

Plasma proteins such as fibrin and fibrinogen also accumulate in atheromata. Meanwhile, the circulating blood and tiny blood vessels in the artery walls (vasa vasorum) continue to supply more fat, cholesterol, connective tissue and cells to fibrous lesions so that the deposits continue to grow. In humans, by the mid-thirties and early forties, atherosclerotic deposits are seen throughout the vascular tree and can become calcified, as chalky minerals accumulate that fill in the fibrous scar tissue. Most young adults have atherosclerotic plaque not only in the heart vessels, but also along the entire length of the ascending aorta, leading toward the brain, and along the iliac and femoral arteries nourishing the organs in the pelvic region. These complicated lesions set the stage for stroke, heart attack or peripheral vascular disease. In addition to narrowing the arteries, atherosclerotic plaque may ulcerate and form thrombi, which are made up chiefly of coagulated blood platelets.

A variety of stimuli, including high blood pressure, high blood sugar (diabetes), acute inflammation, poisonous chemicals like tobacco components, and even stress may make atherosclerotic fat deposits (plaques) unstable. This is particularly true when plaques are rich in fat (cholesterol) and white blood cells (inflammatory cells). An unstable plaque may crack or rupture and expose its contents to flowing blood. In its own defense, the body attempts to heal this injury by forming a blood clot over the damaged area. The formation of a blood clot occurs in several steps. First, platelets adhere to the ruptured plaque surface. They then begin to stick together in a process known as aggregation. The growing platelet aggregate forms a surface on which the process of coagulation can occur: through a series of enzymatic reactions involving serine proteases, a net-like substance (fibrin) forms, linking platelets together, red blood cells are trapped within the fibrin meshwork, and a blood clot results.

Blood clots may form when blood circulation is slowed, or they may develop around atheromata and cause an active, acute obstruction of the arteries. An embolus, or detached thrombus, can also drift downstream to smaller-diameter blood vessels where it may eventually become lodged like a boulder in a stream. When this happens, blood supply may be completely shut off, producing an infarction, or localized death, of a segment of the brain, the heart muscle, the lungs, the legs or the feet. Other complications may also result from the buildup of atherosclerotic plaque. When tissue in the wall of an artery under an atheroma bleeds, hemorrhaging may result. An abscess, or localized infection, may also develop beneath the hardened deposit, leading to injury and disease.

Blood clots can be especially dangerous for patients with heart disease. A heart attack (myocardial infarction) results when a blood clot interrupts or blocks blood flow to the heart, which starves the heart muscle of oxygen and causes heart muscle cells to die; the same process in the brain causes a stroke (cerebral infarction).

Vascular cells become multi-functional at the interface of thrombosis and inflammation with accumulating evidence linking inflammatory responses to pro-thrombotic stimuli. Endothelial cells provide both a barrier and link between activation of coagulation and innate immune pathways. Inflammation shifts the endothelial cell balance from an anti-thrombotic state to a pro-coagulant state, with accompanying conversion of pro-enzymes to active serine proteinases in the clotting cascade. Activated serine proteinases promote adhesion and activation of platelets on the endothelial cell surface through the expression of adhesion molecules. Adhesion molecules expressed on the endothelial cells, as part of a pro-coagulant response, recognize, bind and decelerate leukocyte motion in the blood stream and support emigration of leukocytes into the vessel wall. The transmigrated leukocytes are activated and express inflammatory molecules that promote plaque development. Activated leukocytes also promote the production and activation of matrix metalloproteinases (MMPs), which degrade extracellular matrix proteins and results in plaque instability and rupture. Unstable ruptured plaque exposes of the underlying necrotic contents to the circulating blood, causing arterial occlusion (heart attacks and strokes) and progression of plaque growth, atherothrombosis.

Exposure of the inner plaque core after rupture or erosion introduces the plaque collagen and lipids to the cells in the circulating blood and also exposes tissue factor a key mediator of the extrinsic clotting cascade and a known linking protease for clot formation and inflammatory responses. With exposure of the highly thrombotic plaque core contents, platelets, monocytes and T cells are activated resulting in further platelet activation, fibrin deposition and activation of monocytes/macrophages with a continuing cascaded of actions leading to vessel occlusions.

Thrombotic and inflammatory responses in cells are accompanied by surface receptor reorganization and structural alterations in cellular membranes, which are reflected in microviscosity (the reciprocal of membrane fluidity) changes of the amphipathic lipid bilayer. Altered membrane fluidity has been detected in many disease states, e.g, thrombocythaemia, hyperlipidimia, hypercholesterolaemia, hypertension, diabetes mellitus, obesity, sepsis, and acute coronary syndromes are among others. (Zalai et al., *J Am Coll Cardiol* 2001, 38:1340-47). Optimal conformation of membrane-associated receptors protects membrane's function and is maintained by specific microviscosity conditions. Accordingly, membrane fluidity acts as a marker in defining the activation state of a cell.

Serine proteinase inhibitors ("serpins") make up a superfamily of related proteins and have been found encoded by poxviruses from four different genera. The myxoma viral secreted serine proteinase inhibitor, SERP-1, inhibits the thrombolytic proteases urokinase- and tissue-type plasminogen activators (uPA and tPA respectively) and plasmin in vitro and has demonstrated profound anti-inflammatory activity in a wide range of animal models. (U.S. Pat. No. 5,686,409; U.S. Pat. No. 5,917,014; U.S. Pat. No. 5,939,525; Nash et al., *J. Biol. Chem.* 1998, 273: 20982-91; Lomas et al., *J. Biol. Chem.* 1993, 268: 516-21; Lucas et al., *Circulation* 1996, 94: 2694-2705; Lucas et al., *J Heart Lung Transplant* 2000, 19:1029-1038; Miller et al, *Circulation* 2000, 101:1598-1605; Bot et al., *Circ. Res.* 2003, 93: 464-471; Brahn et al., *American College of Rheumatology Meeting*; Nov. 13-17, 1999; Boston; Bedard et al., Abstract 1143, *American Society of Transplant Surgeons* 2002; Wang et al., Abstract, *7th International Congress of Xenotransplantation* 2003; Nash et al., *J Biol Chem* 1998, 273(33): 20982-91; Dai et al., *J of Biol Chem* 2003, 278(20): 18563-72).

Since platelets play a key role in the body's response to injury in an artery and in beginning the process of forming a blood clot, interrupting that process has become an important part of the battle against heart disease and stroke. Antiplatelet therapy drugs can interfere with platelet function and are classified into 3 categories: Those that prevent cardiovascular diseases (primary prevention), those that treat an acute disease, and those that treat a chronic disease (secondary prevention). There are both oral and intravenous drugs that inhibit platelet function and are used to treat patients with cardiovascular and cerebrovascular diseases. Three types of antiplatelet agents have been used as medical products: aspirin, ADP receptor antagonists (clopidogrel and ticlopidine) and glycoprotein IIb/IIIa inhibitors (abciximab, integrilin and tirofiban). Their effectiveness, however, is widely variable and there remains a significant clinical unmet need. These agents while preventing acute thrombosis in native atherosclerotic disease or after intervention (angioplasty and stent implant) have limited anti-inflammatory activity. The ADP receptor antagonists and glycoprotein IIb/IIIa antagonists do not prevent atherosclerosis nor restenosis after angioplasty or stent implant. Aspirin and plavix reduce thrombtic occlusion in unstable plaque leading to stroke and myocardial infarctions but many patients are still admitted with unstable coronary and acrotid syndromes with associated progression to MI, CVA or PVO (peripheral vascular occlusion suggesting that the anti-inflammatory actions of ASA are only partially effective in preventing disease progression. This is especially true in the aforementioned diseases where available therapy is either of limited effectiveness/route of administration or is accompanied by unwanted side effect profiles. Thus, there is a need for a safe, effective clinical agent for antiplatelet/antithrombosis therapy.

It has been discovered in accordance with the present invention that SERP-1 displays anti-thrombotic and anti-platelet activities in mammals.

SUMMARY OF THE INVENTION

It is an object of the present invention to provide a novel antithrombotic/antiplatelet agent and a method for inhibiting, treating or preventing thrombosis and embolism in mammals, particularly, in mammals with associated anti-inflammatory actions. The present invention thus provides an important advance in the therapy of thrombosis and embolism related to cardiovascular diseases or abnormal conditions, such as heart attack and stroke.

Accordingly, one aspect of the present invention provides a method for inhibiting or treating or preventing platelet adhesion/aggregation and/or thrombus formation. Specifically, the present invention is directed to antiplatelet therapy in a mammal by administering an effective amount of SERP-1, SERP-1 analogs or biologically active fragments thereof to the mammal.

In one aspect, the present invention provides a method for treating cardiovascular diseases or abnormal conditions related to thrombosis and/or embolism in a mammalian subject. In accordance with the present invention, SERP-1, SERP-1 analogs or biologically active fragments thereof is administered to a subject in need of such treatment for a time under conditions sufficient to treat the cardiovascular diseases or abnormal conditions.

In another aspect, the present invention provides a method of preventing cardiovascular diseases or abnormal conditions in a mammalian subject involving thrombosis and/or embolism, comprising administering a pharmaceutically effective amount of SERP-1, SERP-1 analogs or biologically active fragments thereof to the subject, particularly a subject having a chronic cardiovascular disease or abnormal condition or at a risk of having a cardiovascular disease or abnormal conditions involving thrombosis and/or embolism or a subject with cardiovascular disease who experiences acute interventions (such as angioplasty, stent placement, or vascular bypass surgery), for a time under conditions sufficient to prevent the cardiovascular diseases or abnormal conditions.

In still another aspect, the present invention provides an antiplatelet pharmaceutical composition comprising SERP-1, SERP-1 analog, or biologically active fragment thereof.

In a particular aspect, the present invention provides a method of treating intravascular thrombosis and embolism with coronary, cerebral, or peripheral (limb) infarction, including, but not limited to, heart attack, stroke, gangrene, and ischemia of internal organs such as related to renal, hepatic and intestine infarctions, and pulmonary infarctions or embolism, AV fistula thrombosis as for chronic dialysis patients, peripheral bypass thrombosis, coronary and carotid bypass thrombosis, with the pharmaceutical composition of the invention, or a functional or chemical derivative thereof.

In a further aspect, the present invention provides a kit comprising packaging material and the pharmaceutical composition of the present invention within the packaging material and wherein the pharmaceutical composition is effective for antiplatelet activity and wherein the packaging material comprises a label which indicates that the pharmaceutical agent is an antiplatelet agent.

BRIEF DESCRIPTION OF THE DRAWINGS

FIG. 1A depicts adhesion of platelets isolated from human blood to fibronectin with saline or SERP-1 (500 ng/mL) treatments and thrombin activated platelets with Saline or SERP-1 (500 ng/mL). SERP-1 reduced adhesion of both thrombin activated and non-activated platelets reaching significance (p=0.005) in non-activated platelets. FIG. 1B depicts adhesion of platelets to collagen III with saline or SERP-1 (500 ng/mL) treatments and thrombin activated platelets with Saline or SERP-1 (500 ng/mL). SERP-1 showed a reducing trend (p=0.09) towards adhesion of thrombin activated platelets to collagen III but not non-activated platelets (p=0.824). FIG. 1C depicts adhesion of PBMCs isolated from human blood to Fibronectin and collagen III with saline or SERP-1 (500 ng/mL) treatments. SERP-1 a showed reducing trend (p=0.09) towards adhesion of PBMCs to collagen III, but significantly reduced adhesion of PBMCs (p<0.0.001) to fibronectin.

FIG. 2A-F depict core membrane fluidity measured using lipid membrane probe 1,3-Bispyrenylpropane. FIGS. 2A-2B demonstrate that Endothelial cell's membrane fluidity increased when activated with urokinase, rtPA (recombinant tissue-type plasminogen activator) or PMA for an hour and not thrombin. SERP-1 normalizes the fluidity altered by urokinase, rtPA and PMA significantly. FIGS. 2C-2D demonstrate that urokinase and PMA significantly increased membrane fluidity in THP-1 cells. SERP-1 attenuates activation against both urokinase and PMA. FIGS. 2E-2F demonstrate that urokinase alone altered membrane fluidity in T-cells and SERP-1 normalized the activation.

FIGS. 4A and 4B compare SERP-1 and PAI-1 in the treatment of aortic allografts in which a segment of aorta from a PAI-1 deficient (PAI-1−/−) C57B1/6 mouse was transplanted into a wild-type (PAI-1+/+) Balb/c mouse. FIG. 4A shows that the area of plaque development was measured in transplanted mice that were treated with either saline, Serp-1, analogs of Serp-1 in which the residues reactive center were mutated so that the protein could not function as a proteinase inhibitor (SAA and Ala6), or so that it was homologous to other serpins (DC, NM, PAI-2). In this case, treatment with Serp-1 showed a marked reduction in plaque formation. FIG. 4B shows that the effect on mortality was measured in the transplanted mice that were treated with either saline, Serp-1, inactive analogs of Serp-1 (SAA), mutant forms of Serp-1 (D294A, D294E), or other serpins (Serp-2, CrmA, ratPAI-1, mouse PAI-1). Note that there is a normal mortality among the transplanted mice of approximately 20%. However, Serp-1 showed a significant reduction in mortality. Importantly, transplanted mice treated with PAI-1 showed 100% mortality, and investigation revealed this was due to thrombosis in the vasculature.

DETAILED DESCRIPTION OF THE INVENTION

Figure 2A:
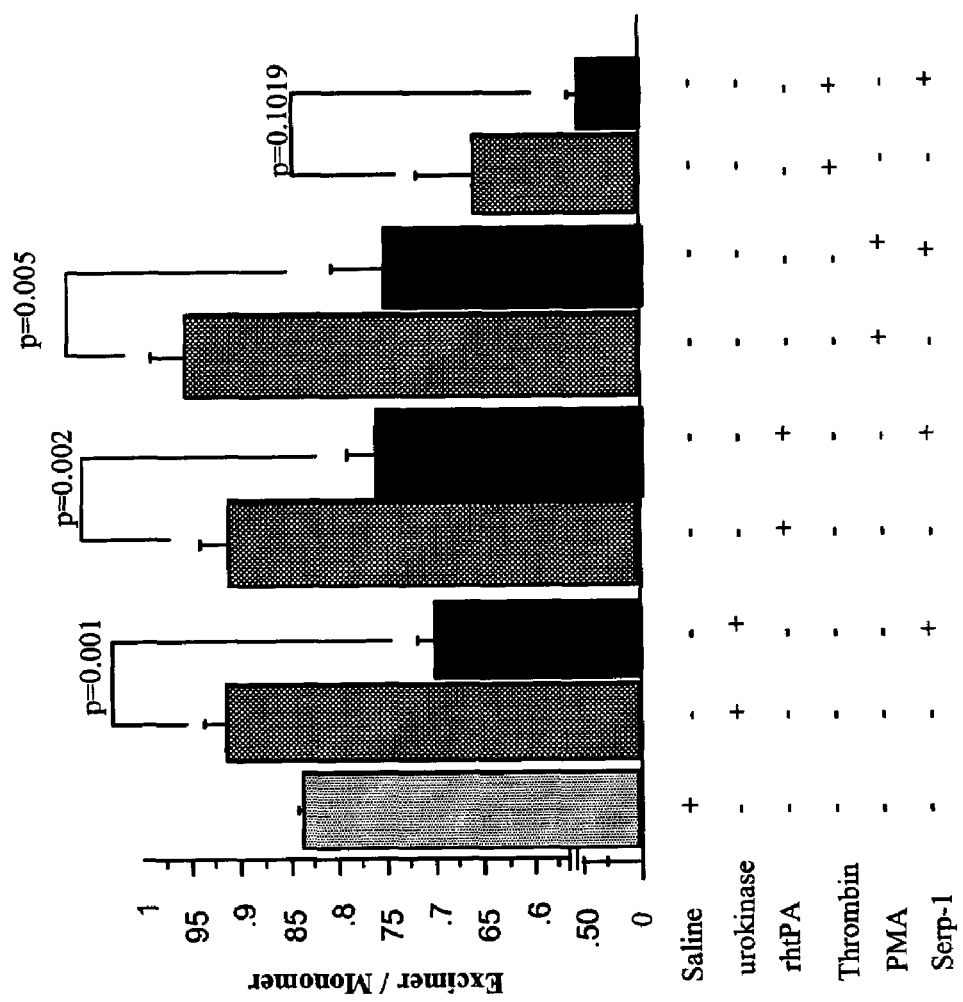

It is an object of this invention to provide compositions and methods for anti-thrombotic and antiplatelet therapy. The present invention is based on a surprising discovery that the protein SERP-1, a serine protease inhibitor ("serpin") produced by malignant rabbit fibroma virus (MRV) and myxoma virus (MYX) with known highly potent anti-inflammatory activities, its analogs and biologically active fragments thereof, not only binds to and inhibits enzymes that are active in clot lysis (clot break down or fibrinolysis), but also displays unexpected anti-thrombotic and anti-platelet activities in mammals.

Specifically, the present invention recognizes that SERP-1 can inhibit adhesion and activation of platelets. It has been discovered in accordance with the present invention that SERP-1 treatment alters expression of selected genes in the inflammatory pathway in human endothelial cells. Moreover, it has also been discovered in accordance with the present invention that SERP-1 displays a unique capacity to modulate platelet, endothelial cell and mononuclear cell activation with associated regulation of intracellular calcium.

By "antiplatelet" or "antiplatelet activity" is meant interfering, impairing or inhibiting the ability of platelets activation and/or aggregation and formation of a platelet plug leading to thrombosis and/or embolism (blood cloting). An antiplatelet agent is an agent that possesses or exhibits antiplatelet ability. An antiplatelet agent is a type of anti-thrombotic agents, which are most useful in treating and preventing clinical states due to arterial vascular diseases and thrombotic events caused by inflammation.

By "antiplatelet therapy" is meant any means that is useful for preventing/treating thromboembolic artery occlusions in cardiovascular diseases or abnormal conditions. For the purpose of present invention, the term is used interchangeably with antithrombotic (drug) therapy.

Specific serine proteinase inhibitors ("serpins"), including SERP-1 and PAI-1, act as links between the thrombotic pathway and the innate immune response or inflammation pathways. Serpins that target the plasminogen activators and plasmin (clot dissolving enzymes) have the potential to be pro-thrombotic by inhibiting artery clot lysis by serine proteinases, such as uPA and tPA. Despite its pro-thrombotic activity, PAI-1, a human serpin that targets tPA and uPA, has been shown to reduce plaque growth in selected animal models. PAI-1 has however also been found to inhibit clot lysis after treatment of clots with plasminogen activators and to initiate a pro-thrombotic state in clot forming models in animals. Conversely, SERP-1 markedly attenuates macrophage invasion and plaque growth in a wide range of animal models of atherosclerosis and transplant rejection with no increase in thrombosis. However, as demonstrated by the Examples herein, when PAI-1 deficient mouse aorta was transplanted into normal (PAI-1 expressing) mice, PAI-1 infusion caused acute vascular thrombosis with 100% early mortality. In contrast, SERP-1 did not increase thrombosis and showed no evidence for inhibiting clot lysis), SERP-1 also significantly reduced plaque growth (only 10-20% mortality, which is norm for any mouse aortic transplant), thereby exhibiting no pro-thrombotic activities. See FIG. 4A and FIG. 4B.

Accordingly, one embodiment of the present invention provides a method for inhibiting or treating or preventing platelet adhesion/aggregation and/or thrombus formation. Specifically, the present invention is directed to antiplatelet therapy in a mammal by administering an effective amount of SERP-1, SERP-1 analogs or biologically active fragments thereof to the mammal.

Serine proteinase inhibitors (i.e., serpins) maintain haemostasis through regulation of thrombotic and thrombolytic proteases. According to the present invention, SERP-1 can effectively attenuate or inhibit platelet and circulating mononuclear cell adhesion to matrix proteins, fibronectin and collagen.

In accordance with the present invention, the SERP-1 protein, SERP-1 analog or biologically active fragment thereof, is first obtained and purified in accordance with the teaching of U.S. Pat. Nos. 5,686,409 and 5,939,525, whose teachings are incorporated herein by reference.

After purification to a semi-pure or preferably to the more highly purified state, SERP-1 can then be admixed with sterile water and saline or other pharmaceutically acceptable carrier to a concentration in the range of between about 1 pg/ml and about 50 mg/ml and preferably between about 1 pg/ml and about 1 µg/ml. Alternatively, the SERP-1, SERP-1 analog, or biologically active fragment thereof, can be stored as a lyophilized powder, or frozen, and then later solubilized in sterile water or saline or other pharmaceutically acceptable carrier to the above delineated concentrations.

The SERP-1 of the present invention can be administered to a human patient preferably as a pharmaceutical composition in a therapeutically effective amount. The term "therapeutically effective amount" means the dose needed to effectively inhibit/treat/prevent platelet activation/adhesion/aggregation or thrombus formation. The pharmaceutical compositions of the present invention contain a therapeutically effective dose of the SERP-1 protein, homologs or analogs thereof or else contain a biologically active fragment of the SERP-1 protein, homologs or analogs thereof, or SERP-1 coding sequence in a virus, or a nucleotide sequencing encoding SERP-1 and a pharmaceutically acceptable carrier.

As used herein, "analogs" is meant to include substitutions or alterations in the amino acid sequence of the SERP-1 protein, which substitutions or alterations (e.g., additions and deletions) maintain the anti-platelet properties of the protein when delivered to the site of platelet activation/adhesion/aggravation or thrombus formation either directed at the site, i.e. locally, or systemically.

For purposes of the present invention, the term "analog" includes amino acid insertional derivatives of SERP-1 such as amino and/or carboxyl terminal fusions as well as intrasequence insertions of single or multiple amino acids. Insertional amino acid sequence variants are those in which one or more amino acid residues are introduced into a predetermined site in the protein. Random insertion is also possible with suitable screening of the resulting product. Deletional variants are characterized by removal of one or more amino acids from the sequence. Substitutional amino acid variants are those in which at least one residue in the sequence has been removed and a different residue inserted in its place. Where the protein is derivatized by amino acid substitution, amino acids are generally replaced by other amino acids having similar physical chemical properties such as hydrophobicity, hydrophilicity, electronegativity, bulky side chains and the like. Examples of conservative substitutions include the substitution of a non-polar (hydrophobic) residue such as isoleucine, valine, leucine or methionine for another. Likewise, the present invention contemplates the substitution of a polar (hydrophilic) residue such as between arginine and lysine, between glutamine and asparagine, and between glycine and serine. Additionally, the substitution of a basic residue such as lysine, arginine or histidine for another or the substitution of an acidic residue such as aspartic acid or glutamic acid for another is also contemplated.

As used herein, the term "analogs" also encompasses homologs of SERP-1, i.e., corresponding amino acid sequences derived from other SERP-1 proteins and having the same or substantially the same anti-platelet properties. As used herein, the term "biologically active fragments" refer to fragments of SERP-1 or SERP-1 analogs which do not encompass the entire length of the SERP-1 polypeptide but which nevertheless maintain the anti-platelet properties of the entire SERP-1 polypeptide or analogs thereof when delivered to the site of platelet activation/adhesion/aggregation or thrombus formation either at the site (i.e. locally) or systemically.

SERP-1 amino acid variants can be readily made using peptide synthetic techniques well known in the art such as solid phase peptide synthesis (Merrifield synthesis) and the like or by recombinant DNA techniques well known in the art. Techniques for making substitution mutations at predetermined sites in DNA include for example M13 mutagenesis. Manipulation of DNA sequences to produce substitutional, insertional, or deletional variants are conveniently described elsewhere such as Sambrook et al., *Molecular Cloning: A Laboratory Manual*, Cold Spring Harbor Laboratory, 1989.

For purposes of the present invention, analogs of SERP-1 also include single or multiple substitutions, deletions and/or additions of any component(s) naturally or artificially associated with the SERP-1 such as carbohydrate, lipid and/or other proteinaceous moieties. All such molecules are encompassed by the term SERP-1 analogs.

In one embodiment of the invention, in order to increase the specific activity of the prepared SERP-1 protein, the cysteine residue at position 244 can be substituted with another amino acid residue, for example alanine. Such a substitution can cause the SERP-1 protein to be more biologically active since Cys244 is the predicted position for SERP-1 dimer formation through disulfide bridges. Because Cys244 lies very close to the reactive center of the SERP-1 protein, SERP-1 dimers are thought to have a disturbed and obfuscated reactive center thereby rendering them biologically inactive. Lomas et al., 1993 J. Biol. Chem. 268 (1): 516-521. A mutation at position 244 can prevent the formation of SERP-1 dimers in the production of SERP-1 through recombinant DNA means. A decrease in the presence of SERP-1 dimers in a preparative sample is useful since the specific activity of the isolated protein will be increased and thus less protein will be needed in a pharmaceutical preparation. The inhibitory activity of serpins on serine proteinases is believed to revolve around the slow dissociation of the serpin from the serine protease after cleavage of the serpin between the P1 and P1' residues in the active region. Upton et al., 1990 *Virology* 179: 618-631. The amino acid sequence Arg/Asp has been located at the predicted SERP-1 P1-P1' site (amino acid residues 319 and 320) and is the predicted site for cleavage by serine proteases. Substitutions of either or both of these two amino acids produces SERP-1 analogs of varying biological activities useful in the practice of the present invention.

Endothelial cells provide a pivotal regulatory point for SERP-1 mediated anti-inflammatory functions. According to the present invention, it has also been discovered that SERP-1 treatment alters expression of selected genes in the inflammatory pathway in mammalian endothelial cells. Changes in intracellular calcium regulating genes and restoration of homeostatic calcium concentrations accompany the SERP-1 mediated calming or ameliorating of cellular activation responses. Thus, SERP-1 displays a unique capacity to modulate platelet, endothelial cell and mononuclear cell activation with associated regulation of intracellular calcium.

Key enzymes involved in coagulation and inflammation pathways are calcium dependant. Activation of factors II, IX and X and fibrin polymerization in the thrombotic pathway and result in activation of PKC (protein kinase C), MAPK (Mitogen Activated Protein Kinase) and Ras in inflammatory pathway, among others. Intracellular calcium stores are in part regulated by inositol-1,4,5-triphosphate ($IP_3$). Activation of cells with receptors activates phospholipase C (PLC) through tyrosine kinases. PLC generates $IP_3$ through hydrolysis of $PIP_2$ which then binds to the $IP_3$ receptor ($IP_3R$) on the endoplasmic reticulum/sarcoplasmic reticulum and releases calcium from intracellular stores. Hydrolysis of $PIP_2$ by PLC also forms diacylglycerol (DAG) which, in combination with calcium, activates PKC and catalyses various cellular functions. PLC generates $PIP_3$ through activation of $PI_3$-kinase that associates with GTPase activating protein which then activates Ras, and triggers MAPK pathways.

As described in Example 3 below, SERP-1 can concomitantly normalize activation of endothelial cells treated with urokinase (p=0.001), rtPA (p<0.002), or PMA (p<0.005), activation of THP-1 cells treated with urokinase (p=0.003) and PMA (p<0.001) and activation of T lymphocytes treated with urokinase (p=0.030). SERP-1 can also restore changes in cellular membrane fluidity to baseline levels. By maintaining normal calcium levels and baseline level of membrane fluidity of the aforementioned cells, SERP-1 reduces and/or inhibits the activation/adhesion of these cells and thereby subsides or inhibits both inflammatory and coagulatory responses.

Without intending to be limited by any particular mechanism, it is believed that SERP-1 can modulate activation of endothelial cells by regulating expression of key enzymes involved in the coagulation process. It is believed that such modulation is implemented through normalizing intracellular calcium of cells, such as platelets and endothelial cells. For example, it is reported that an increase in intracellular calcium can result in a conformation change in the glycoprotein IIb/IIIa receptor thereby activating platelets, allowing platelets to bind to fibrinogen. It is further believed that by maintaining normal calcium levels in platelet, endothelial cells and T lymphocytes, SERP-1 can reduce or inhibit activation/adhesion/aggravation of platelet and the activation of endothelial cells and T lymphocytes in coagulation responses.

Accordingly, another embodiment of the present invention provides a method for modulating the immune response in a mammal by employing SERP-1, its analogs or biological active fragments thereof, to alter expression of the genes in the inflammatory pathway in the endothelial cells of the mammal, particularly, through restoration of homeostatic calcium concentrations. As a result, the activation of platelets, endothelial cells and mononuclear cells are modulated.

Another embodiment of the present invention provides a method for treating cardiovascular diseases or abnormal conditions in a mammalian subject involving thrombosis and/or embolism. In accordance with the present invention, SERP-1, SERP-1 analogs or biologically active fragments thereof is administered to a subject in need of such treatment for a time under conditions sufficient to treat the cardiovascular diseases or abnormal conditions.

In another embodiment, the present invention provides a method of preventing cardiovascular diseases or abnormal conditions or their recurrence in a mammalian subject involving thrombosis and embolism, comprising administering a pharmaceutically effective amount of SERP-1, SERP-1 analogs or biologically active fragments thereof to a mammalian subject, particularly a subject having chronic cardiovascular diseases or abnormal conditions, or a subject who is determined to be at a risk of having a cardiovascular disease or abnormal condition based on genetic predispositions or clinical diagnosis, for a time under conditions sufficient to prevent the cardiovascular diseases or abnormal conditions.

For purposes of the present invention, the term “treat”, “treating” or “treatment” includes preventing, inhibiting, reducing the occurrence of and/or ameliorating the physiological effects involving thrombosis and/or embolism in mammals, including but not limited to humans.

By “cardiovascular diseases” is meant any impairment of normal functioning relating to the heart, blood vessels (arteries, veins, and capillaries) and blood, which include, but are not limited to, coronary diseases and cerebrovascular diseases. By “cardiovascular abnormal condition” is meant a condition or state of being or occurrence in heart, blood vessels (arteries, veins, and capillaries) and blood of a mammal that is aberrant from a normal mammal of the same species and sex under the same living conditions, even though the there is no detectable impairment of normal functioning of the heart, blood vessels and blood. For example, risk factors, such as diabetes, smoking and sedentary life style, can cause undetectable physiological changes (abnormal conditions) leading to blood clotting or coronary disease. A “cardiovascular abnormal condition” also includes, but is not limited to, coronary angioplasty.

More specifically, in accordance with the present invention, a therapeutically effective amount of SERP-1, SERP-1 analogs or biologically active fragments thereof is administered to a subject in need of such treatment for a time and under conditions sufficient to treat, for example, stroke. The term “subject” as used in the present invention is taken to mean any mammalian subject or patient to which the compositions of the invention can be administered. Subjects specifically intended for treatment or prevention with the compositions and methodologies of the present invention include humans, as well as non human primates, sheep, horses, cattle, goats, pigs, dogs, cats, rabbits, guinea pigs, poultry, hamsters, rats and mice, as well as the organs, tumors and cells derived or originating from these hosts. The present invention, therefore, is useful for treatment or prevention of a variety of clinical cardiovascular diseases or abnormal conditions involving thrombosis and/or embolism, such as coronary angioplasty and acute myocardial infarction including stroke.

A further embodiment of the present invention provides a method of treating or preventing cardiovascular diseases or abnormal condition in a subject in need, comprising administering the subject a pharmaceutically effective amount of SERP-1, SERP-1 analogs or biologically active fragments thereof in combination with at least one other antiplatelet agent, including but not limited to, aspirin, clopidogrel (e.g., plavix), ridogrel, ticlopidine, and glycoprotein IIb/IIIa inhibitors (e.g., abciximab, integrilin, lamifiban, tirofiban and xemlofiban).

Having been used as a medical product for over 100 years, aspirin is the cornerstone of treatment for patients with any vascular disease. Although aspirin is not advised for most healthy people to prevent a first heart attack or stroke, it does offer some protection for older (>50 years of age) individuals at high risk, including smokers or those with diabetes or a family history of atherosclerotic disease at an early age. In studies involving more than 100,000 patients, aspirin has been shown to reduce the risk of dying from a heart attack or stroke when it is given in the early hours after symptoms begin. Patients who undergo invasive procedures such as coronary angioplasty/stenting or coronary artery bypass surgery also benefit from aspirin. Given before and after these procedures, it reduces the risk of heart attack and stroke. Once a patient has had a heart attack, a stroke, or an episode of chest pain (angina), daily treatment with aspirin substantially reduces the risk of a second heart attack or stroke. Although the benefits of prolonged aspirin use are now well known by healthcare providers, the optimal dose of aspirin is unknown. There is evidence to support dosages that range from a baby aspirin or less (81 mg) through a full standard aspirin (325 mg). Because there are no definite dosing data, most cardiologists recommend 160 to 325 mg as a daily dose and accept a dose of 81 mg/d as enough for patients who have side effects with higher doses.

Accordingly, in a particular embodiment, the present invention contemplates that the daily dosage of aspirin of to be administered with SERP-1 is about 81 mg to about 325 mg.

Clopidogrel is a relatively new drug that reduces the risk of vascular events when it is given with aspirin to patients who have unstable chest pain or angina or certain types of heart attacks. When taken regularly after a heart attack or stroke, its benefits are similar to those of aspirin. Clopidogrel works by interfering with one of the ways that platelets stick together.

By studying families who have an inherited disorder of their platelets, investigators have learned that platelets stick together by binding a protein in the blood (fibrinogen), to a certain site on the surface of the platelet, the glycoprotein IIb/IIIa receptor complex. Blocking fibrinogen's ability to bind to the glycoprotein IIb/IIIa receptor dramatically interferes with what platelets typically do, thus decreasing blood clotting. The drugs that do this are the glycoprotein IIb/IIIa inhibitors, and they are specific examples of drugs that are designed to interfere with a specific biological process (in this case, platelet function). The glycoprotein IIb/IIIa inhibitors are given intravenously to patients who are undergoing coronary angioplasty/stenting or to high-risk patients with unstable angina or a particular type of heart attack. Their benefits have been especially noteworthy with coronary angioplasty, where they reduce the occurrence of acute complications (death, heart attack, or the need for an urgent second procedure, such as bypass surgery). However, efforts have been unsuccessful to find an oral form of these drugs.

According to the present invention, Serp-1 is advantageous over the above-mentioned available antiplatelet agents. In particular, the present invention recognizes that Serp-1 combines both anti-inflammatory and anti-platelet activities, both of which are important for treatment of vascular diseases, and has minimal side effects.

A yet further embodiment of the present invention provides a method of treating or preventing cardiovascular diseases or abnormal conditions, comprising administering a subject in need a pharmaceutically effective amount of SERP-1, SERP-1 analogs or biologically active fragments thereof in combination with at least one anti-coagulent, including but not limited to heparin and warfarin, or a pharmaceutically effective amount of SERP-1, SERP-1 analogs or biologically active fragments thereof in combination with at least one other antiplatelet agent and further in combination with at least one anti-coagulent.

In another embodiment, the present invention provides an antiplatelet pharmaceutical composition comprising SERP-1, SERP-1 analog, or biologically active fragment thereof.

In a particular embodiment, the present invention provides a method of treating intervascular thrombosis and embolism cerebral infarction, including but not limited to heart attack, stroke, gangrene, and ischemia of internal organs such as related to renal, hepatic and intestine infarctions, and pulmonary infarctions or embolism, AV fistula thrombosis as for chronic dialysis patients, peripheral bypass thrombosis, coronary and carotid bypass thrombosis, with the pharmaceutical preparation of the invention, or a functional or chemical derivative thereof.

In a further aspect, the present invention provides a kit comprising packaging material and the pharmaceutical composition of the present invention within the packaging material and wherein the pharmaceutical composition is effective for antiplatelet activity and wherein the packaging material comprises a label which indicates that the pharmaceutical agent is an antiplatelet agent. The compositions and methodologies of the present invention are also efficacious in the treatment of cardiovascular diseases and abnormal conditions.

In the aforementioned embodiments of the invention, the SERP-1, SERP-1 analog or biologically active fragment thereof is delivered in a manner consistent with conventional methodologies associated with the treatment of, for example, coronary diseases and angioplasty. Such delivery methods contemplate, for example, intravenous, intra-articular, intrarectal, intraperitoneal, intramuscular, subcutaneous, or aerosol inhalantion to prevent or treat or inhibit thrombosis and/or blood clotting associated with such diseases and/or abnormal conditions. According to the present invention, SERP-1 or SERP-1 in combination with at least one other antiplatelet agent can treat acute diseases and chronic diseases (secondary prevention) related to thrombosis and blood clotting.

The formulation of pharmaceutical compositions is generally known in the art and reference can conveniently be made to *Remington's Pharmaceutical Sciences,* 17th ed., Mack Publishing Co., Easton, Pa. Formulation of the SERP-1 protein, analogs, or fragments thereof for use in the present invention must be stable under the conditions of manufacture and storage and must also be preserved against the contaminating action of microorganisms such as bacteria and fungi. Prevention against microorganism contamination can be achieved through the addition of various antibacterial and antifungal agents.

The pharmaceutical forms of SERP-1 suitable for infusion include sterile aqueous solutions or dispersions and sterile powders for the extemporaneous preparation of sterile injectable solutions or dispersion. In all cases, the form must be sterile and must be fluid to the extent that easy syringability exists. Typical carriers include a solvent or dispersion medium containing, for example, water buffered aqueous solutions (i.e., biocompatible buffers), ethanol, polyols such as glycerol, propylene glycol, polyethylene glycol, suitable mixtures thereof, surfactants, or vegetable oils. Sterilization can be accomplished by any art-recognized technique, including but not limited to filtration or addition of antibacterial or antifungal agents, for example, paraben, chlorobutanol, phenol, sorbic acid or thimerosal. Further, isotonic agents such as sugars or sodium chloride can be incorporated in the subject compositions.

Production of sterile injectable solutions containing the subject SERP-1 is accomplished by incorporating the compounds in the required amount in the appropriate solvent with various ingredients enumerated above, as required, followed by sterilization, preferably filter sterilization. To obtain a sterile powder, the above solutions are vacuum-dried or freeze-dried as necessary.

The SERP-1 protein or analogs and fragments thereof, are thus compounded for convenient and effective administration in pharmaceutically effective amounts with a suitable pharmaceutically acceptable carrier in a therapeutically effective dose.

As used herein, the term "pharmaceutically acceptable carrier and/or diluent" includes any and all solvents, dispersion media, antibacterial and antifungal agents, microcapsules, liposomes, cationic lipid carriers, isotonic and absorption delaying agents and the like which are not incompatible with the active ingredients (SERP-1, SERP-1 analogs and fragments thereof). The use of such media and agents for pharmaceutical active substances is well known in the art. Supplementary active ingredients can also be incorporated into the compositions and used in the methods of the present invention.

The precise therapeutically effective amount of SERP-1 to be used in the methods of this invention applied to humans can be determined by the ordinarily skilled artisan with consideration of individual differences in age, weight, extent of cellular infiltration by inflammatory cells and condition of the patient. It can generally be stated that the SERP-1 pharmaceutical preparation of the present invention should be preferably administered in an amount of at least about 1 pg/kg to about 5 g/kg per infusion dose, more preferably in an amount of about 5 µg/kg to about 50 mg/kg per dose.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly depend on the unique characteristics of the active material (e.g., SERP-1 protein) and the limitations inherent in the art of compounding such an active material for the treatment of transplant rejection as herein disclosed in detail.

The principal active ingredients are compounded for convenient and effective administration in effective amounts with a suitable pharmaceutically acceptable carrier in dosage unit form as hereinabove disclosed. A unit dosage form can, for example, contain the principal active compound in amounts ranging from about 5 µg/kg to about 500 mg/kg.

Packaging material used to contain the SERP-1 active ingredient can comprise glass, plastic, metal or any other suitable inert material so long as the packaging material does not chemically react with any of the ingredients contained therein.

The SERP-1 protein, analogs or fragments thereof can be administered in a manner compatible with the dosage formulation and in such amount as will be therapeutically effective. The compositions of the invention can be administered in any way which is medically acceptable which can depend on the disease condition or injury being treated. Possible administration routes include injections, by parenteral routes such as intravascular, intravenous, intra-arterial, subcutaneous, intramuscular, intratumor, intraperitoneal, intraventricular, intraepidural or others, as well as oral, nasal, ophthalmic, rectal, topical, or by inhalation. The compositions can also be directly applied to tissue surfaces during surgery. Sustained release administration is also specifically included in the invention, by such means as depot injections or erodible implants.

The invention is further illustrated by the following specific examples which are not intended in any way to limit the scope of the invention.

EXAMPLE 1

This example provides an analysis of comparative effects of SERP-1 with the mammalian serpin PAI-1 that also targets tPA and uPA, but not plasmin.

Methods: PAI-1 deficient C57B1/6 mouse aorta was transplanted into normal Balb/c mice with SERP-1, PAI-1 or saline infusion. Cell adhesion and migration assays were performed in 96-well plates and Boyden chambers respectively. Monocyte, T cell and endothelial cell (HUVEC) activation states were assessed by pyrene based membrane fluidity assay. SERP-1 and PAI-1 mediated changes in gene expression were analyzed by microarray and confirmed by RT-PCR analysis.

Results: In the mouse aortic allograft transplant model, PAI-1 and not SERP-1 caused acute vascular thrombosis with 100% early mortality. SERP-1 markedly reduced plaque growth in this model similar to findings in ApoE mice, rats, rabbits and microswine. Infusion of viral serpins that do not bind tPA, uPA and plasmin (Serp-2 and CrmA) showed no effect on thrombosis or plaque growth. PAI-1 reduced the bleeding time in Balb/c mice whereas SERP-1 did not. SERP-1 reduced THP-1 monocyte adhesion to endothelial monolayers and differed from PAI-1 in attenuating adhesion of platelets and Peripheral blood mononuclear cells to Fibronectin. On microarray analysis of HUVECs, SERP-1 altered expression of tPA, SNX 10, FGF1, Factor 13A1, JAM3, Col 6A and AVEN.

Conclusion: The anti-inflammatory viral serpin, SERP-1, that targets thrombolytic enzymes display beneficial anti-inflammatory activity in animal models and human cells with no adverse thrombotic effect. SERP-1 treatment also alters expression of selected genes in the inflammatory pathway in endothelial cells.

EXAMPLE 2

Methods: PAI-1 deficient C57Bl/6 mouse aorta was transplanted into normal Balb/c mice with SERP-1, PAI-1 or saline infusion. SERP-1 and PAI-1 mediated change in gene expression of endothelial cells was analyzed by microarray and confirmed by RT-PCR analysis. Platelets and PBMC's were isolated from peripheral blood and adhesion to fibronectin in the presence of SERP-1 and PAI-1 was assessed. Mouse tail bleeding time was measured after SERP-1 and PAI-1 infusion. Monocyte, T cell and endothelial cell (HUVEC) activation states were assessed by pyrene based membrane fluidity assay.

Results: In the mouse aortic allograft transplant model, PAI-1 and not SERP-1 caused acute vascular thrombosis with 100% early mortality for PAI-1 and <10% for SERP-1. SERP-1 markedly reduced plaque growth (p<0.001) in this model similar to findings in ApoE mice, rats, rabbits and microswine. PAI-1 (1.15±0.067 min) reduced the bleeding time in Balb/c mice whereas SERP-1 (2.358±0.269 min) did not. SERP-1 differed from PAI-1 in attenuating adhesion of platelets and peripheral blood mononuclear cells. The active site mutants of Serp-1 tested had no effect on thrombosis, bleeding or inflammatory cell reactions in these models and did not reduce plaque growth suggesting that Serp-1 mediated antiplatelet and anti-inflammatory effects are unique to the Serp-1 molecule. On microarray analysis of HUVECs, SERP-1 altered expression of tPA, SNX 10, FGF1, Factor 13A1 and JAM3.

Conclusion: The anti-inflammatory viral serpin, SERP-1, that targets thrombolytic enzymes display beneficial anti-inflammatory activity in animal models and human cells with no thrombotic activity, i.e., platelets' adhesion/aggravation is reduced or inhibited. SERP-1 treatment alter expression of selected genes in the inflammatory pathway in human endothelial cells.

EXAMPLE 3

To understand the cellular targets for SERP-1, this Example studied the effects of SERP-1 on adhesion and activation of circulating platelets and peripheral blood mononuclear cells from normal volunteers as well as endothelial, monocyte and lymphocyte cells. Associated changes in intracellular calcium were measured and regulation of gene expression in endothelial cells assessed by microarray analysis.

Materials and methods: 1,3-Bis(1-pyrenyl)propane (BPP) and 1-(4-trimethylaminophenyl)-6-phenyl-1,3,5-hexatriene 4-toluenesulfonate (TMA-DPH), Calcein AM and Fura-2AM were purchased from Molecular Probes Inc., Eugene, Oreg., USA and urokinase (H.Mwt) from American Diagnostica, rtPA (Alteplase, rtPA; Cathflo) from Hoffmann-l, a Roche Ltd., Mississauga ON and Thrombin (Thrombostat) from Parke-Davis Div., Warner-Lambert Canada Inc., Scarborough, ON. Phorbol-12-myristate-13-acetate and other chemicals used in the study were procured from Sigma-Aldrich Chemicals Ltd., Oakville, ON, Canada unless otherwise mentioned. Viral protein, SERP-1 was kindly provided by Viron Therapeutics Inc., London, ON. Cell Cultures—Human Umbilical Vein Endothelial Cells were obtained from Bio Whittaker and the cells were cultured with Bullet Kit (Clonetics, Walkersville, Md., USA). The cells at fourth to sixth passages were used in this study. The human monocytic cell line, THP-1 (TIB-202) and T-lymphocyte, Jurkat cells, E6.1 clone (TIB-152) were procured from American Type Culture Collection, Rockville, Md., USA and were cultured in RPMI medium supplemented with 10% Fetal Bovine Serum (Invitrogen Canada Inc., Burlington, ON), Penicillin (1 U/ml) and Streptomycin (1 mg/ml) (Invitrogen Canada Inc., Burlington, ON) and with added 2% L-Glutamine and 1% Sodium Pyruvate for Jurkat T lymphocytes. Cells were maintained at a confluence of one million per ml.

Isolation of PBMC's and platelets: For circulating peripheral blood mononuclear cell isolation, blood was collected in vacutainers containing 0.057 ml of 15% EDTA (B. D Falcon) from healthy volunteers (n=1). 15 ml of anti-coagulated blood was mixed with 15 ml of PBS with 3% FBS and placed carefully over 15 ml of Ficoll paque plus (Amersham Pharmacia Biotech AB, Upsala, Sweden) and centrifuged at 1000 g for 30 min at room temperature (Beckman Instrument Inc., Palo Alto, Calif.). Mononuclear cells were harvested from the interface and washed twice with PBS.

For platelet isolation, blood was collected in vacutainers containing 0.5 ml of 3.8% sodium citrate buffer, blood was centrifuged at 800 g for 5 min, the top platelet rich plasma (PRP) layer was removed and platelets were isolated by spinning PRP at 2000 g for 12 min. The isolated platelets were washed with sodium citrate and EDTA wash buffer (NaCl 90 mM, KCl 5 mM, Trisodium citrate 36 mM, Disodium EDTA 10 mM, Glucose 5 mM adjusted to pH 6.5) and resuspended in incubation buffer (NaCl 134 mM, NaHCO$_3$ 12 mM, KCl 2.9 mM, Na$_2$HPO$_4$ 0.34 mM, MgCl$_2$ 1 mM, Hepes 10 mM, Glucose 5 mM, BSA 0.3%, pH 7.4).

Adhesion assay: Peripheral blood mononuclear cells and platelets were labelled with Calcein Acetoxy Methyl ester (Calcein AM) (5 µM) for one hour and then treated with either thrombin (1 U/mL) or saline for an hour. Excess fluorescent probe and activators were removed by washing with PBS and resuspended in medium. Cells were subsequently treated with SERP-1 (500 ng/mL) or saline and 0.1 mL cells were placed in fibronectin (5 µg) or collagen III (1 µg) coated 96-well, black plate. After one hour, non adherent cells were removed with two cold PBS washes and adherent cells were quantified by calcein fluorescence (Exc 485 nm/Em 527 nm) using spectrofluorometer (Thermolab systems, Oy,).

Membrane fluidity Studies: One million viable (>95%) THP-1 and T cells or 5×10$^5$ Human umblical vein endothelial cells were labelled with 1,3-bis(pyrenyl)propane (0.8 µM) or 1-(4-trimethylammoniumphenyl)-6-phenyl-1,3,5-hexatriene (TMA-DPH 500 nM) three hours prior to cell activation. Cells were activated with uPA (3 U/mL), recombinant human tPA (rhtPA) (1 µg/mL), Thrombin (1 U/mL) or Phorbol Myristate Acetate (PMA) (1.6 nM/mL) for an hour. Cells were then washed with PBS and resuspended in medium and treated with SERP-1 (500 ng/mL) for one hour. (All centrifugations were carried out at room temperature to avoid temperature influenced alterations in membrane fluidity). Controls were run with dimethyl sulfoxide or saline according to the solvent used for dissolving the individual cell activators. At the end of one hour, cells were washed to remove excess BPP, resuspended in PBS and distributed into 96-well black plates. Monomer and excimer fluorescence emission intensities were measured at 390 nm and 485 nm during excitation at 320 nm using a fluorescent dual wavelength reader (Fluoroskan, Thermolab systems, Oy). Excimer to monomer ratios were measured in triplicate and significance assesses by Analysis of Varience (Statview).

Intracellular Calcium measurement: Cells were washed with buffer (145 mM NaCl, 5 mM KCl, 1 mM MgCl$_2$, 2.5 mM CaCl$_2$, 10 mM HEPES and 10 mM Glucose; pH=7.4), loaded with 3 µM fluorophor Fura-2/AM and treated with individual cell activators for one hour. Activators were then washed off, cells were resuspended in Krebs HEPES buffer (18.3 mM NaCl, 25 mM NaHCO$_3$, 3.5 mM KCl, 2.5 mM CaCl$_2$, 0.1 mM MgCl$_2$, 1.2 mM MgSO$_4$, 1.2 mM KH2PO$_4$, 117 mM Glucose and 10 mM HEPES (pH 7.4). See Calcium Signaling Protocols, 1999, Humana Press, Totowa, N.J. ed: David G. Lambert, page 31-39) and placed in 96-well black plate (Garnier bio-one, Longwood, Fla.). SERP-1 (500 ng/mL) was added to the appropriate wells and emission at 527 nm was measured while exciting at 320 nm (calcium bound Fura-2) and 390 nm (calcium free Fura-2) over one hour at 37° C. Ratio of emission values at 527 nm during excitations 320 and 390 nm was calculated as R. Subsequently Rmax was calculated after disrupting the cells with 2.5 µL 0.1% Triton X-100 and Rmin by adding 5 µL of EGTA (5 µM in 1M NaOH) to sequester all the calcium bound to Fura-2. S$_{fb}$, the correction factor for unbound Fura 2 was calculated from emission at 527 nm with excitation, 390 nm for the free (EGTA added) and calcium bound (Triton X-100 added) Fura-2. The intracellular calcium concentration was calculated using the following formula with K$_d$ value 224 nM (dissociation constant) for Fura 2-AM with calcium at 37° C. (Grynkiewicz et al., *J. Biol. Chem* 1985, Vol. 260, No. 6, pp. 3440-50).

$$[Ca] = \frac{K_d \times (R - R_{min}) \times S_{fb}}{(R_{max} - R)}$$

RNA isolation: HUVECs from IVth passage were treated with Saline or SERP-1 (400 ng/mL) for 4 h and total RNA was extracted using TRIzol (Invitrogen Canada Inc., Mississauga, ON, Canada) reagent. Isolated total RNA was further purified using a Qiagen RNeasy column (Qiagen Inc., Mississauga, Canada) and integrity was confirmed with an Agilent 2100 Bioanalyzer (Agilent Technologies Canada Inc., Mississauga, Canada).

Microarray analysis: Human specific high-density cDNA microslides representing 19,008 genes (Human 19K Arrays) procured from Microarray Centre, ON (Ontario Cancer Institute/Princess Margaret & Hospital/University Health Network, Toronto, ON, Canada) were used to study altered gene expression in HUVECs by SERP-1. For each experiment, treatments were repeated with dye swapping between the control saline and SERP-1 treated samples performed in triplicate. RNA was transcribed to Cy3 or Cy5 labeled cDNA by RT reaction where fluorophors Cy3-dCTP or Cy5-dCTP (Amersham Biosciences Inc., Quebec, Canada) was used along with other dNTPs (MBI Fermentas Inc., Burlington, ON, Canada). Template RNA was hydrolyzed by incubating reaction mixtures with 50 mM EDTA (4 µL) and 10N NaOH (2 µL), neutralized and cDNA precipitated with isopropanol, washed with ethanol, dried and re-suspended in DNAse free water. A pre-hybridization step of 50 mJ UV irradiation was followed by treatment with buffer containing sodium citrate, sodium chloride, 0.1% SDS and 0.2% BSA for 20 min at 50° C., washing with water and drying with nitrogen stream was performed for all the slides. Slides were incubated with DIG Easy Hyb solution (Roche Diagnostics, Quebec, Canada) and cDNA probes from control and treatment at 37° C. for 18 hours in the dark by placing two slides of Human 19K Array facing each other. The slides were then washed with pre-warmed SSC containing 0.1% SDS solution at 50° C., rinsed with water and spun dried at 500 rpm for 5 min followed by drying with nitrogen gas stream. Arrays were scanned immediately.

Microarray slides were scanned using a Virtek scanner (Virtek Vision Corporation., Waterloo, ON, Canada) to measure spot intensity and were normalized using Array Vision (version 5.1, Imaging research Inc., St. Catherines, Onw, Canada). The normalized raw data was imported into Gene Spring software (Version 4.1.2, Silicon genetics Inc., Redwood city, Calif., US) and further analyzed. Genes with ratios greater than 1.5 fold and less than 0.66 fold were considered for further analysis and a p value of 0.05 was used as filter for significance.

Statistics: Differences in membrane fluidity, cellular adhesion and intracellular calcium concentrations were assessed by analysis of variance (ANOVA) and students T-test. A p value of less than 0.05 was considered significant.

Results:

Adhesion of circulating platelets and mononuclear cells to fibronectin and collagen: SERP-1 significantly reduced adhesion of non-activated platelets isolated from normal volunteers to fibronectin (p=0.005). SERP-1 did not however block thrombin activated platelet adhesion to fibronectin (p=0.121) (FIG. 1A). A reducing trend was observed in platelet adhesion to collagen III, both with and without thrombin activation, after treatment of platelets with SERP-1, but such reducing effect was reached significantly only with thrombin activation (p=0.048) (FIG. 1B). SERP-1 also reduced adhesion of normal non-activated peripheral blood mononuclear cells to fibronectin (p<0.001), but failed to reduce adhesion with collagen III (0.09) (FIG. 1C).

Figure 2C:
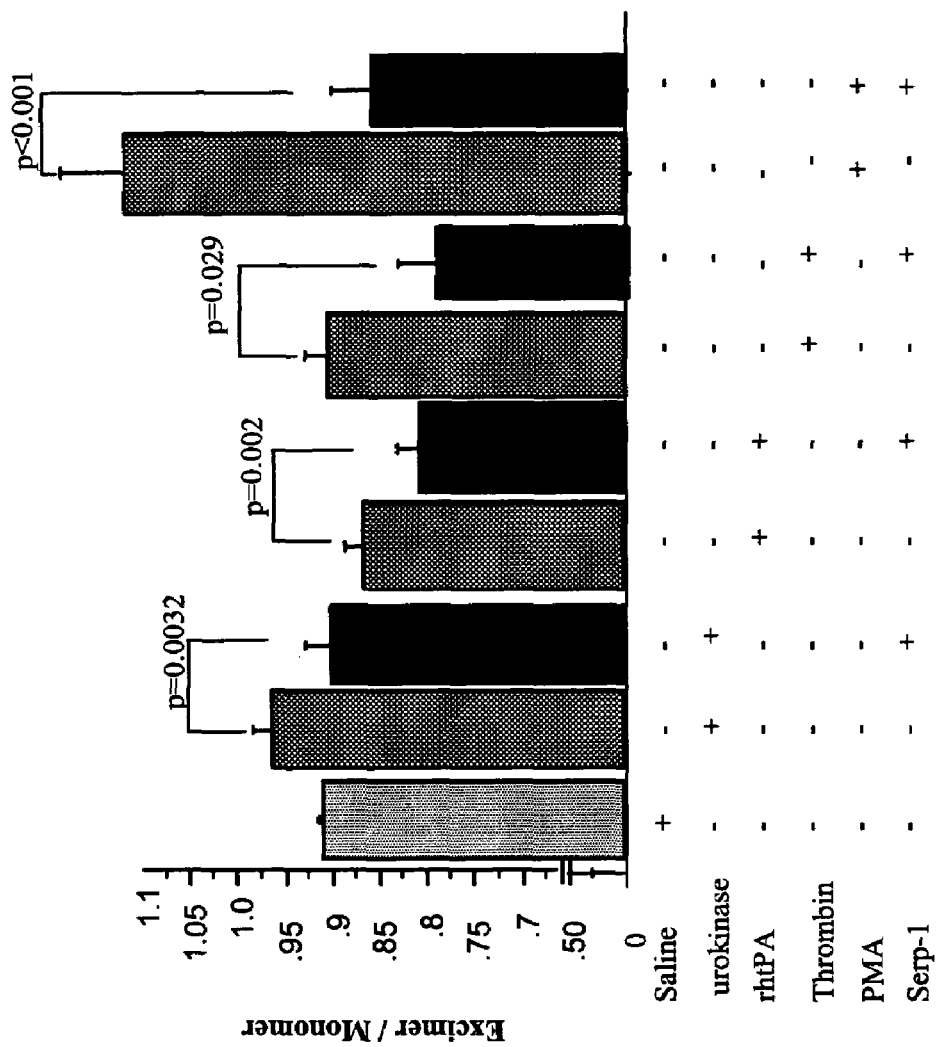
Figure 2D:
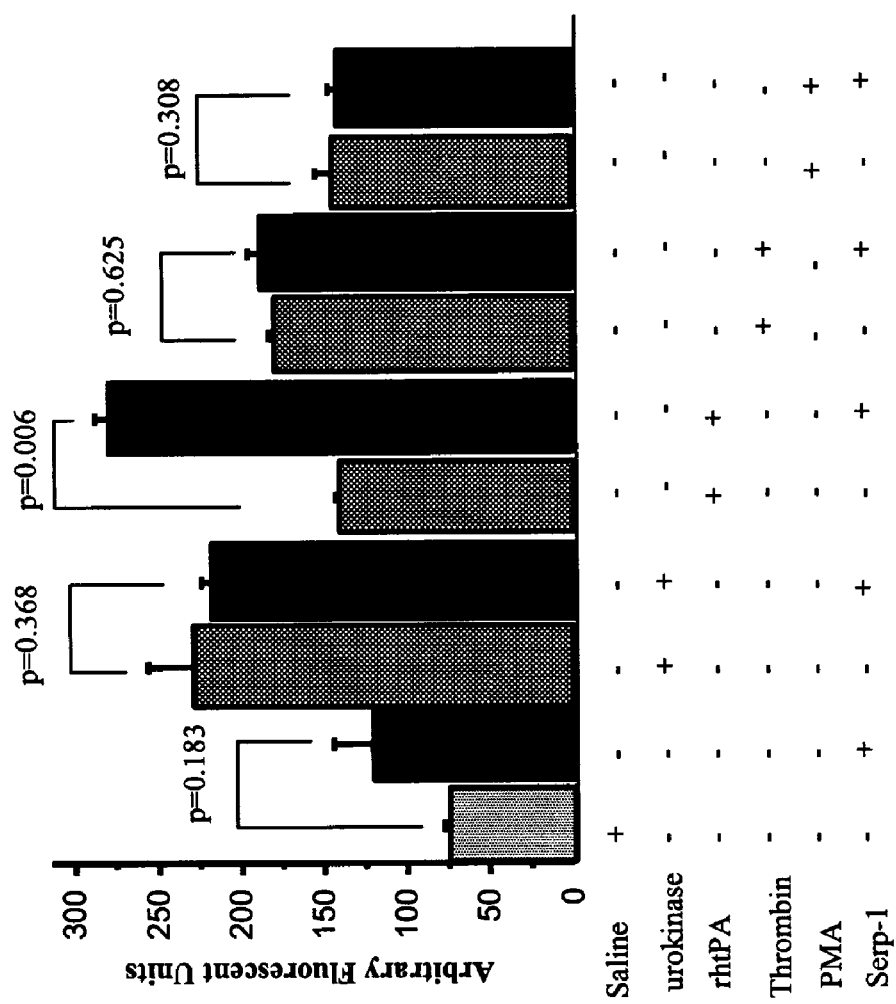

Membrane Fluidity:

Core and surface membrane fluidities of individual cell lines were evaluated by BPP and TMA-DPH respectively after treatment of cells with urokinase, rtPA and PMA. The core membrane fluidity of endothelial cells (HUVEC) increased with urokinase (p=0.031), rtPA (p=0.007) and PMA (p=0.041) and decreased with thrombin (p=0.310) in HUVECs (FIG. 2A). SERP-1 neutralized activation of HUVECs after treatment with urokinase (p=0.001), rhtPA (p=0.002) and PMA (p=0.005) restoring normal fluidity. SERP-1 reduced thrombin activated HUVECs fluidity even further after treatment (p=0.102) but, as noted, thrombin did not significantly alter fluidity compared to control (FIG. 2A). Surface membrane fluidity, as measured by TMA-DPH was not altered by uPA, rtPA and PMA, but surface fluidity was reduced by thrombin (FIG. 2B) (p=0.110). SERP-1 significantly increased the surface fluidity of non-activated HUVECs (p=0.03) and HUVEC treated with uPA, and PMA but not those treated with thrombin. Activation of the monocytic cell line, THP-1 resulted in significant changes in membrane fluidity which were reversed by SERP-1 for selected activating agents. In THP-1 cells, urokinase and PMA increased core fluidity (p<0.015 and p=0.0016, respectively) significantly. rhtPA (p=0.799) and thrombin (p=0.577) treatment failed to alter the fluidity significantly (FIG. 2C) compared to control saline, although showing a trend toward a reduction in membrane fluidity. SERP-1 normalized the changes in core fluidity induced by urokinase (p=0.003) and PMA (p<0.001), and also significantly reduced the fluidity of THP-1 cells after treatment with rhtPA (p=0.002) and thrombin (p=0.03). The surface fluidity was significantly increased with urokinase (p<0.001), rtPA (p=0.030), thrombin (p=0.015) and PMA (p=0.004) activation (FIG. 2D). SERP-1 treatment alone did not alter surface fluidity and did not alter the increased fluidity produced by urokinase (p=0.368), thrombin (p=0.625) and PMA (p=0.308) activated THP-1 cells, but did significantly increase the surface fluidity in rhtPA activated cells (p=0.006).

Figure 2E:
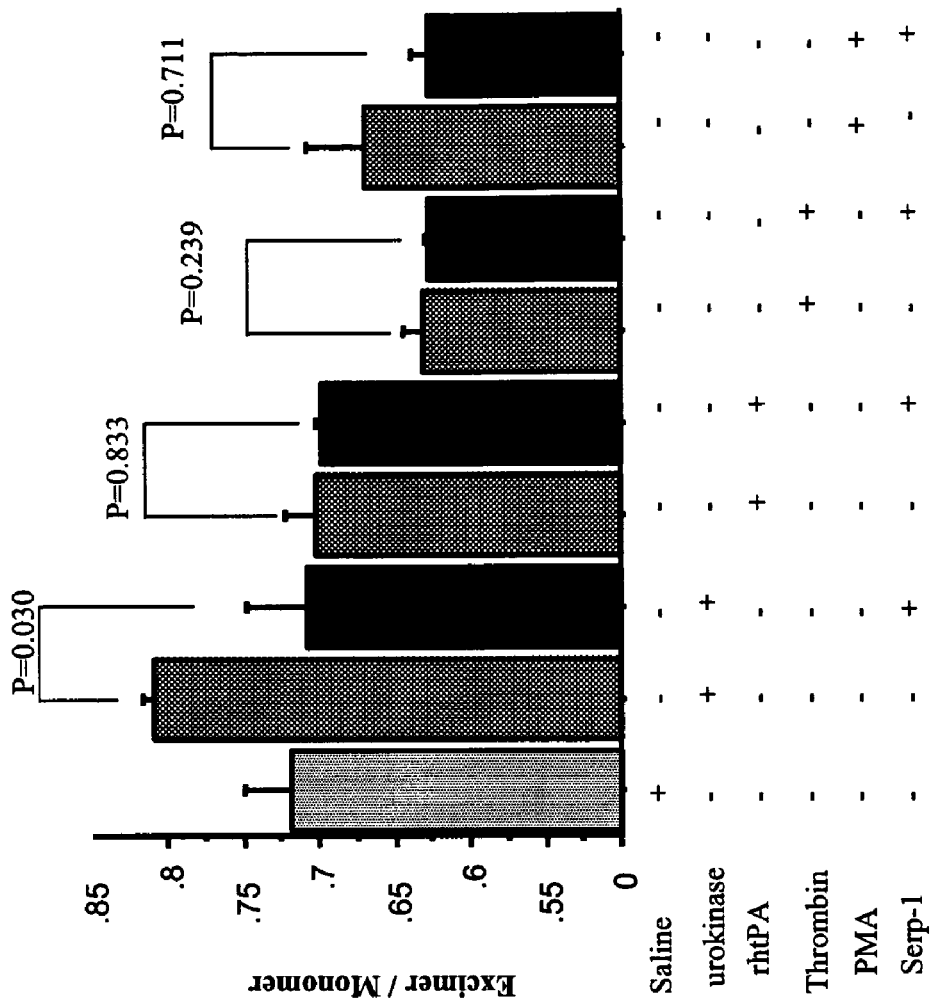
Figure 2F:
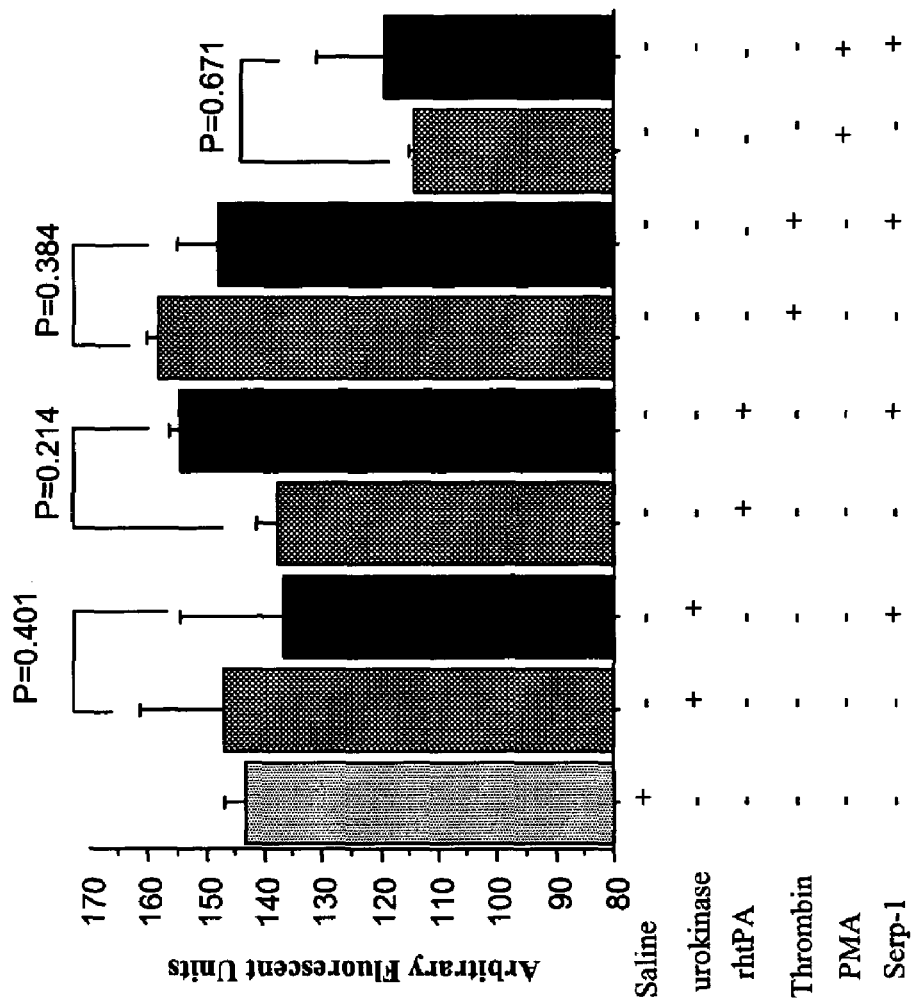

Changes in membrane fluidity were also detected in Jurkat T cells after treatment with SERP-1 and the activating agents. In T-cells, fluidity was increased by urokinase (p=0.044) and decreased by thrombin (p=0.002), but not significantly altered by rtPA (p=0.513) and PMA (p=0.233). SERP-1 prevented the increase in core fluidity in urokinase activated T-cells (p=0.030) but did not significantly alter fluidity after treatment with rtPA (p=0.833), thrombin (p=0.239) or PMA (p=0.711) (FIG. 2E). Surface fluidity of T-cells was significantly increased by thrombin and decreased by PMA, but in this case not altered by rhtPA and urokinase. SERP-1 did not reverse the surface fluidity changes detected after thrombin or PMA treatment (FIG. 2F).

Figure 3A:
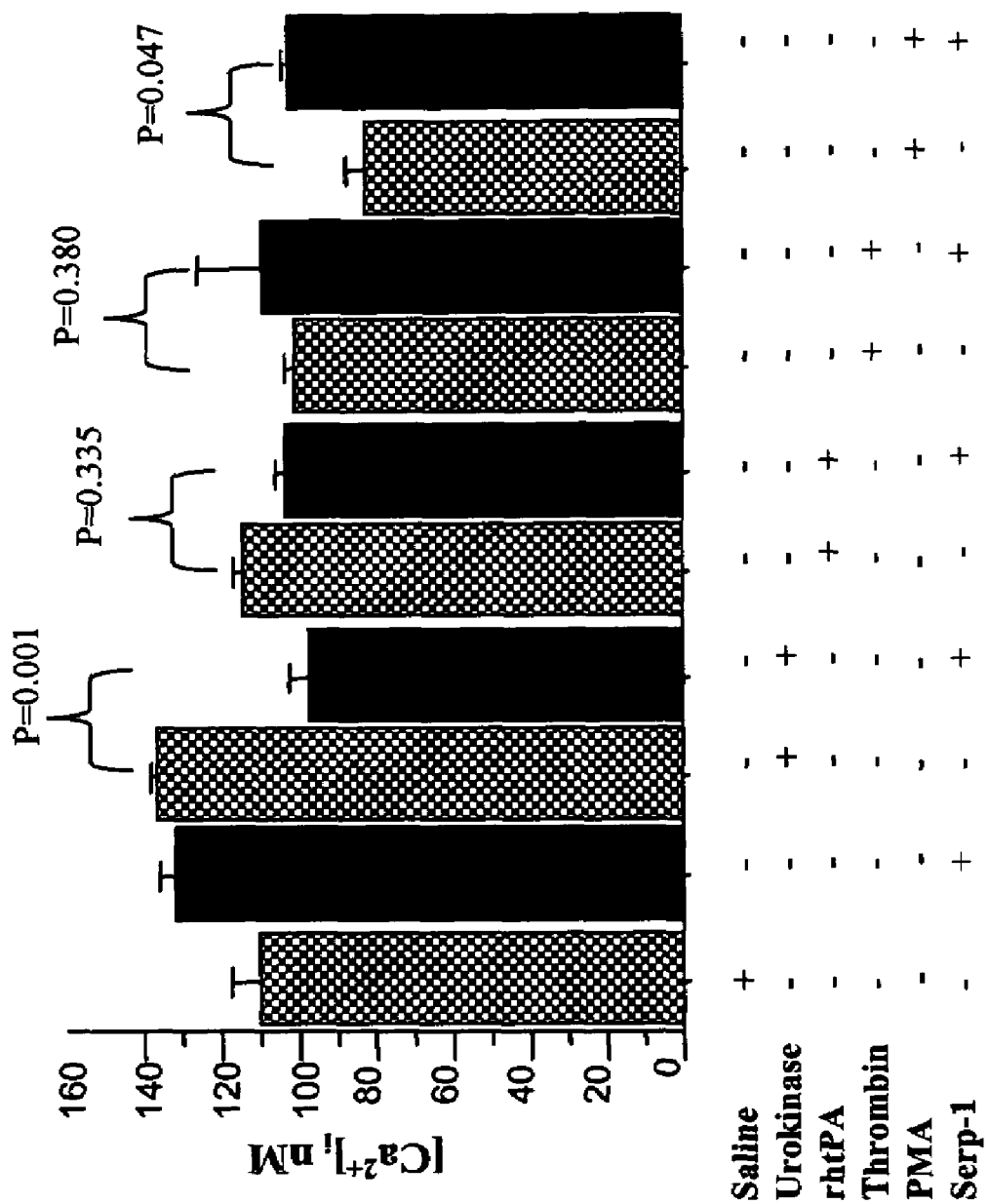
FIGS. 3A-3C depict intracellular calcium measured in Endothelial cells. SERP-1 shows increased [Ca2+]i at resting conditions compared to saline. Activation of HUVECs with HMW (high molecular weight) urokinase increased intracellular calcium and PMA decreased intracellular calcium. SERP-1 counter regulated calcium concentration alterations in these two activation conditions and maintains homeostasis.
Figure 3D:
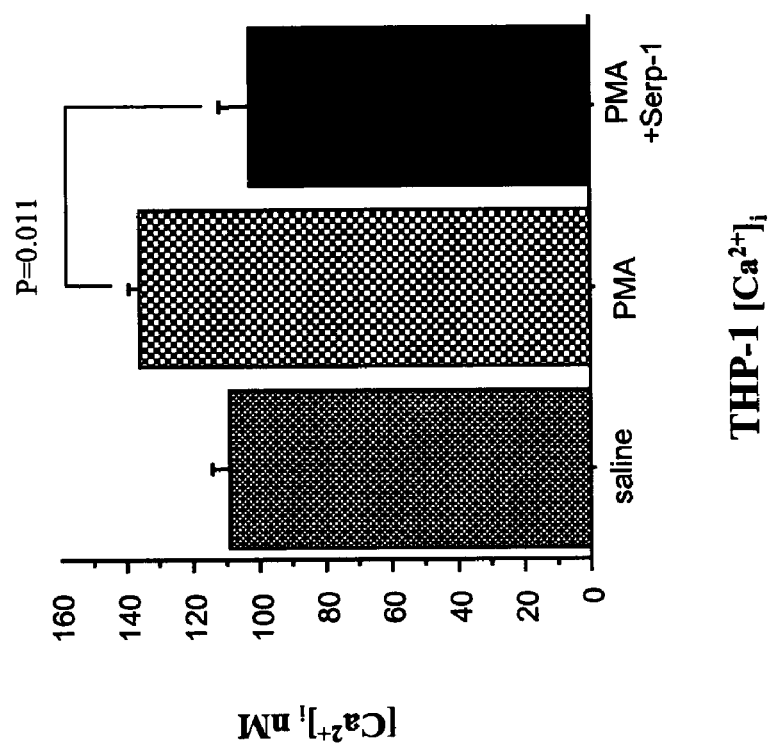
FIGS. 3D-3E depict intracellular calcium concentrations in THP-1 cells with saline, PMA or PMA and SERP-1 treatments. PMA increased intracellular calcium concentration and SERP-1 restored it.
Figure 3E:
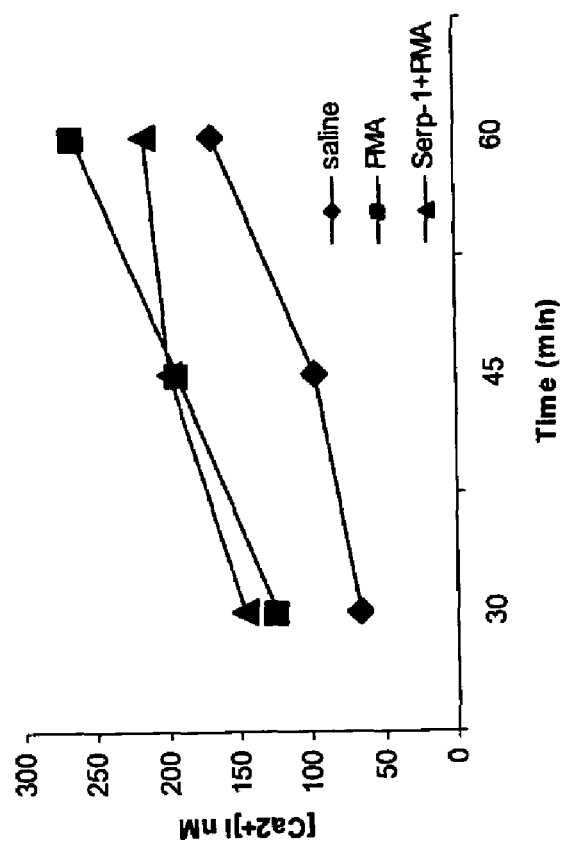
Figure 3F:
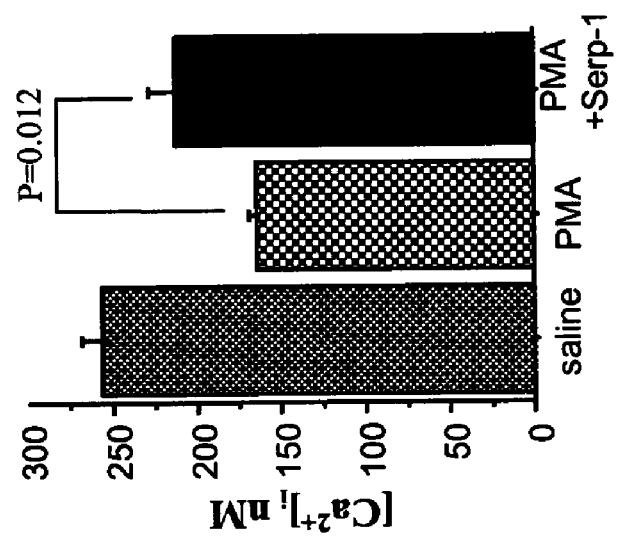
FIG. 3F depicts intracellular calcium concentration in T-lymphocytes treated with saline, PMA or PMA and SERP-1. Phorbol ester decreases the intracellular calcium, but SERP-1 normalizes the intracellular calcium.
Figure 3G:
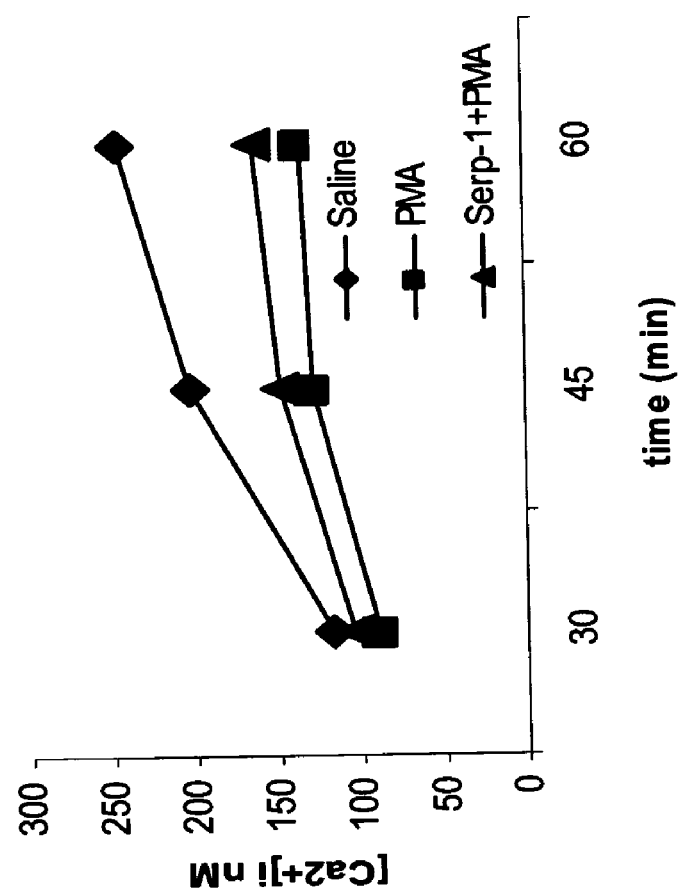

Intracellular Calcium:

Cellular calcium was assessed in endothelial cells, monocytes and T cells after activation with agents demonstrated to alter cellular activation on membrane fluidity assays. Calcium stores were then assessed with activation in the presence and absence of SERP-1 treatment. Changes in intracellular calcium levels were examined over time in HUVEC, monocytes and T cells after treatment with each activating agent. SERP-1 had an immediate early and sustained effect on Ca stores in endothelial cells with a later effect on THP-1 and T cell cultured cells. Intracellular calcium was altered in HUVEC with urokinase and PMA (FIG. 3A) treatments. Urokinase showed an initial increasing and later decreasing trend in $[Ca^{2+}]i$ over an hour (FIG. 3B). Activation was gradual with PMA, where the $[Ca^{2+}]i$ was significantly lowered at all the time points compared to control saline (FIG. 3C). The alterations in $[Ca^{2+}]i$ due to urokinase and PMA was counteracted by SERP-1 that normalized $[Ca^{2+}]i$. In THP-1 cells, PMA increased [Ca2+]i at all time points and in T lymphocytes urokinase decreased the $[Ca^{2+}]i$, where in both cases, SERP-1 restored normal $[Ca^{2+}]i$ (levels FIGS. 3D, 3E, 3G & 3H).

Microarray Analysis:

Gene expression profiles from microarray analysis of HUVEC (Table 1) clearly showed an increase in the expression of PKC (protein kinase C) β1(3.1 fold), calcium/calmodulin dependant serine protein kinase (1.8 fold), inositol-1,4,5-triphosphate receptor typeII (1.6 fold), S100 calcium binding protein A12 (calgranulin C) (1.6 fold) and RAS guanyl releasing protein I (calcium and DAG regulated) (1.6 fold) by SERP-1.

Discussion:

In this series of studies, it has been demonstrated that the viral anti-inflammatory serpin, SERP-1, targets a wide range of cells involved the coagulation and inflammation cascades. Treatment of human platelets, endothelial cells, monocytes and T cells reduced cellular adhesion an activation in response to a series of activators with associated modulation of cellular calcium. SERP-1 initiates an early and sustained normalizing response in HUVEC with associated significant changes in expression of calcium regulating genes.

Trauma to the vascular bed produces an instantaneous response with activation of thrombotic events to prevent haemorrhage. The formation of clot initiates inflammatory cell responses, events triggered by activation of platelets and endothelial cells. Thrombolytic serine proteases are also expressed by endothelial cells, monocytes, lymphocytes and smooth muscle cells, both inhibiting excess thrombosis and activating cell adhesion, migration and invasion to initiate tissue repair responses. Increased in levels of the thrombolytic proteinase uPA, its receptor uPAR and its inhibitor human acute phase serine proteinase inhibitor, PAI-1 have been implicated in various diseases. SERP-1, causes no adverse thrombosis in damaged vessels and has proved to be an effective anti-inflammatory molecule as exemplified from animal studies (Dai et al., *The Journal of Biological Chemistry* 2003, 278(20): 18563-72; Bot et al., *Circulation Research*, 2003, 93:464-71; Lucas and McFadden et al., *Journal of Immunology* 2004, 173: 10 pages (In Press); Zalai et al., *Cardiovascular Plaque Rupture*, Brown D L, Ed, Marcel Dekker, Inc., New York 2002, 447-82), but has not been found to increase thrombosis indicating previously undefined anti-coagulation activities.

When tested adhesion of platelets to fibronectin (FIG. 1A) and collagen (FIG. 1B) SERP-1 significantly reduced adhesion showing that initial activation of platelet exposed to sub-cellular matrix is attenuated by SERP-1. Adhesion of leukocytes to the vascular wall either to endothelial cells or exposed substratum also initiates non-platelet dependent thrombin activation and innate immune responses that results in diapedesis and inflammation. SERP-1 effectively reduced PBMC adhesion to Fibronectin that results in low cellular invasion and attenuated plaque progression. This is in accordance with the observations from an animal study where SERP-1 reduced mononuclear cell invasion associated with plaque reduction. (Dai et al; Bot et al; Lucas and McFadden et al; Zalai et al; Miller et al., *Circulation* 2000, 101:1598-1605; Lucas et al., *Circulation* 1996, 94:2890-2900; Lucas et al., *J. Heart Lung Transplant.* 2000, 19:1029-38). SERP-1 attenuated the activation of Endothelial cells, pro monocytic THP-1 cells and Jurkat T-lymphocytes treated with urokinase, endothelial cells and THP-1 cells activated by PMA and endothelial cell activated by rhtPA (FIGS. 2A, 2B & 2C) as revealed by membrane fluidity studies. PMA activates Protein Kinase C, thrombotic mediators (Thrombomodulin, Tissue Factor (TF), Platelet activating Factor (PAF) and PDGF), immune response and inflammatory mediators, adhesion molecules (E-selectin, ICAM-1, ELAM-1), interlukins (IL-1, 1Ra, 6, 8 and 11), tPA, uPAR, PAI-1, MMP-19, CD-14, PPAR- and signaling molecules involving Ras, IkkB, NFkB and MAPK in endothelial cells and THP-1 monocytes. uPA and tPA bind to their respective receptors on the surface of cells and activate plasmin and MMPs promoting ECM degradation and cell migration. Without intending to be limited by any particular theory, it is believed that by attenuating these activations, SERP-1 demonstrates an elaborate influence on endothelial, monocyte and T-lymphocyte cells that can contribute to its multicellular activity in targeting coagulation and inflammation. SERP-1 also normalized intracellular calcium concentration in platelets, HUVEC, THP-1 and T-lymphocytes after treatment with PMA and HUVEC with urokinase $[Ca^{2+}]i$. PMA imitates DAG and binds PKC isoforms nonspecifically with associated modulation of intracellular calcium concentration and cell signaling. The non-catalytic amino-terminal end of uPA when bound to the uPA receptor (uPAR), accelerates uPAR aggregation on the cell surface. uPAR aggregation increases $[Ca^{2+}]i$ by activating phospholipase C through a tyrosine kinase-dependent mechanism. Intracellular calcium also regulates organization and function of actin filaments by binding to actin binding proteins and calmodulin. Elevated calcium leads to breakdown of actin bundles and loss of microtubules, while decrease in intracellular calcium can decrease dynamic remodeling of actin filament system. Without intending to be limited by any particular theory, it is believed that by maintaining normal calcium levels, SERP-1 reduces the activation of these cells and reduces inflammatory and coagulatory responses.

From microarray data it is clear that SERP-1 regulates genes involved in calcium regulation, signaling and inflammation, which supports the observation of intracellular calcium alteration and in modifying adhesion and activation. PKC β1, calcium/calmodulin dependant serine protein kinase, PLA2 group IVC and inositol-1,4,5-triphosphate receptor type II (IP3R typeII) are involved in calcium release from intracellular stores and regulation, RAS guanyl releasing protein I (calcium and DAG regulated) is a small guanine nucleotide binding protein that mediate cellular growth and differentiation. Ras is localized to inner surface of the membrane and functions as a molecular switch that transmits receptor signals to downstream MAPK cascades. S100 calcium binding protein A12 (calgranulin C) is involved in innate immune response.

Conclusion: This Example demonstrates a broad-spectrum normalization of cells that regulate coagulation and innate immune responses which is mediated by a viral serpin, SERP-1, that targets serine proteinases in the thrombolytic cascade. This serpin based inhibition of platelet, endothelial cell and mononuclear cell responses can have a profound effect on acute and chronic cardiovascular diseases related to thrombosis and/or embolism.

TABLE 1

Genes involved in Calcium regulation and signaling expressed by Serp-1 treated HUVECs from Microarray analysis

| gbid | Calcium regulating genes | Common Name | Fold Change |
| --- | --- | --- | --- |
| R14058 | protein kinase C, beta 1 | PRKCB1 | 3.138103 |
| N92643 | calcium calmodulin-dependent serine protein kinase | CASK | 1.7726922 |
| BG678857 | protein kinase, DNA-activated, catalytic polypeptide | PRKDC | 1.6852348 |
| H83239 | inositol 1,4,5-triphosphate receptor, type 2 | IIPR2 | 1.6529307 |
| R69183 | RAS guanyl releasing protein 1 (calcium and DAG-regulated) | RASGRP1 | 1.6245245 |
| R18880 | calpain 5 | CAPN5 | 1.6119779 |
| R61677 | phospholipase A2, group IVC (cytosolic, calcium-independent) | PLA2G4C | 1.6018027 |
| R02721 | S100 calcium binding protein A12 (calgranulin C) | S100A12 | 1.5879617 |
| R61092 | inositol 1,4,5-triphosphate receptor, type 2 | IIPR2 | 1.5547315 |
| H09903 | calmodulin binding transcription activator 1 | CAMTA1 | −1.51676 |
| T80372 | calciumchannel, voltage-dependent, alpha 2/delta subunit 2 | CACNA2D2 | −1.6742 |
| R32409 | phospholipase A2, group V | PLA2G5 | −1.95724 |

EXAMPLE 4

The Anti-Inflammatory Viral Serpin SERP-1 Inhibits Human Monocyte Cell Activation Background: Imbalance in endothelial, mononocyte and T cell activation initiates early plaque growth and unstable plaque rupture. SERP-1, has demonstrated anti-inflammatory activity, reducing macrophage and T cell invasion early after angioplasty and transplant with late reduction in plaque growth in a wide range of animal models. The present inventors have examined the effects of SERP-1 on human platelet, endothelial cell, monocytes and T-lymphocytes activation.

Methods/Objective: To find a plausible mechanism through which SERP-1 acts to reduce innate immune responses. THP-1 monocyte, Jurkatt T cells, and human umbilical vein endothelial cell (HUVEC) were treated with SERP-1 (600 ng/ml), the vascular serpin, PAI-1(600 ng/ml) or saline control in the presence and absence of phorbol activation. Generalized cell activation and adhesion to activated and non-activated HUVEC monolayers were studied using pyrene based membrane fluidity and flourimetric assays respectively at 1, 12, 24 and 48 hrs. Gene expression of monocytes and endothelial cells was assessed by Microarray and RT-PCR analysis.

Results: SERP-1 prevented HUVECs activation after SERP-1 treatment at all time points significantly, whereas in T-lymphocytes and Monocytes SERP-1 blocked activation at early and later times respectively. SERP-1 prevented activated monocyte adhesion to and migration across HUVEC monolayers (40% reduction, $p<0.0001$). SERP-1 up-regulated genes involved in signaling, protein traffic and protease degradation and down-regulated genes involved in inflammation. In non-activated monocytes, SERP-1 up-regulated genes involved in translation and down-regulated genes involved in cell adhesion and chemotaxis ICAM-1 expression and PECAM. In HUVECs, SERP-1 modulated the expression of genes involved in signaling and transcription.

Conclusion: Inflammatory responses initiate events leading to plaque growth and rupture. The anti-inflammatory viral serpin, SERP-1, blocks activation of human endothelial cells, monocytes and T cells with associated changes in pro-inflammatory gene expression.

EXAMPLE 5

SERP-1 Sequentially Alters Membrane Fluidity in Activated Human Atherogenic Cells Background: Atherosclerosis is characterized by cell adhesion, rolling, migration and diapedesis. During these processes the morphology of the cells is altered to a great extent, which is also reflected in changes in membrane fluidity. Membrane fluidity is a measure of lateral diffusion and influences important membrane functions such as the conformation and thus the activity of membrane associated enzymes and receptors which are involved in a wide range of functions like cell signalling, proliferation. Phorbol Myristate Acetate (PMA) activation of Endothelial, Monocyte and T-lymphocyte cells express proatherogenic molecules, which could be used as a possible in vitro atherogenic model. The present inventors have studied the effects of a viral Serpin, SERP-1 that blocks plaque growth in animal models of angioplasty and transplant induced vasculopathy on human cellular activation.

Objective: To study the effect of PMA on membrane fluidity of HUVEC’s, human monocytes (THP-1) and Jurkat T-lymphocytes at sequential times and evaluate the action of SERP-1 on these activated cells.

Method: The Cells were activated with PMA (1 ug/ml) for an hour and treated with and without SERP-1 (600 ng/ml) for sequential times. After which, the cells were washed and labelled with Bis Pyrenyl Propane for 18 hours. The excimer to monomer ratio (495 nm/376 nm) was measured using Helium-Cadmium laser (320 nm) as the excitation source.

Results: Endothelial cells showed increased fluidity at earlier time points and later became constricted. Monocytes showed reduced fluidity at all time points studied. T-lymphocytes had reduced fluidity earlier and later this increased.

SERP-1 counter acted the altered fluidity of cells induced by PMA. In HUVEC's SERP-1 reversed the activation at all time points significantly (<0.05). In T-lymphocytes and Monocytes SERP-1 showed significant alteration at early and later time points respectively.

Conclusion: SERP-1 has clearly demonstrated anti-inflammatory properties in animal models. This study demonstrates SERP-1 action on human atherogenic cells exhibiting different degrees of inhibition of PMA induced activation.

EXAMPLE 6

Regulation of Vascular Innate Immune Responses by Vial and Mammalian Serpins

Methods: SERP-1, PAI-1 as well as CrmA and Serp-2 (viral serpins with anti-apoptotic activity), and a series of SERP-1 active site chimeras were given to mice after aortic transplant using PAI-1 deficient C57B1/6 donor mice and wild-type Balb/c recipient mice. The present inventors have also examined human endothelial, monocyte and T cell activation responses by analysis of pyrene based membrane fluidity assays and altered gene expression (Afymetrix microarray and RT-PCR analysis). These changes were correlated with monocyte cell adhesion to endothelial monolayers.

Results: In the mouse model of PAI-1-null aortic transplant, SERP-1 reduced plaque growth while crmA increased plaque growth significantly. Human PAI-1 caused an acute thrombotic response with increased mortality (100% early death) while SERP-1, the SERP-1/serpin chimeras, crmA and Serp-2 when compared to saline control did not increase mortality (10-20% death). SERP-1 normalized changes in membrane fluidity in response to phorbol activation and blocked monocyte adhesion to endothelial cells. PAI-1 and SERP-1 had independent effects on gene expression in monocytes, with SERP-1 increasing expression of TNFa (1.5-2_) and filamin B (5_), but reducing expression of mannosyl (alpha 1,3)-glycoprotein beta 1,4N acetylglucosaminyltransferase (16_), cFos and cathepsin G by 1.5-2 fold. SERP-1 also altered SPs, serpin, chemokine, matrix, FGF, and TGF related gene expression in endothelial cells. See FIGS. 4A-4B.

Conclusions: Viruses have tapped into highly conserved serpin mediated cell defense systems to control inflammatory responses. SERP-1 blocks inflammatory cell responses in animal models without prothrombotic activity and alters cell activation and gene expression in human cell lines.

What is claimed is:

1. A method of inhibiting platelet activation in a mammalian subject, comprising administering a therapeutically effective amount of serine proteinase inhibitor-1 (SERP-1, SERP-1 analog, or biologically active fragment thereof and a pharmaceutically acceptable carrier to said subject, wherein said SERP-1 analog, or biologically active fragment thereof inhibits thrombolytic proteases urokinase-type plasminogen activator, tissue-type plasminogen activator, and plasmin in vitro.

2. A method of inhibiting platelet aggregation in a mammalian subject, comprising administering a therapeutically effective amount of serine proteinase inhibitor-1 (SERP-1), SERF-1 analog, or biologically active fragment thereof and a pharmaceutically acceptable carrier to said subject, wherein said SERF-1 analog, or biologically active fragment thereof inhibits thrombolytic proteases urokinase- type plasminogen activator, tissue-type plasminogen activator, and plasmin in vitro.

3. A method of inhibiting thrombus formation in a mammalian subject comprising administering a therapeutically effective amount of seine proteinase inhibitor-1 (SERP-1), SERP-1 analog, or biologically active fragment thereof and a pharmaceutically acceptable carrier to said subject, wherein said SERP-1 analog, or biologically active fragment thereof inhibits thrombolytic proteases urokinase- type plasminogen activator, tissue-type plasminogen activator, and plasmin in vitro.

4. The method of any one of claims 1, 2, or 3, wherein said mammalian subject is human.

5. The method of any one of claims 1,2, or 3, wherein said SERP-1, SERP-1 analog or biologically active fragment thereof, is delivered by oral administration, intravenous, intra-arterial, intra-articular, subcutaneous, intraperitoneal, intraspinal, intrarectal, or intramuscular infusion or aerosol inhalant.

* * * * *